(12) United States Patent
O'Hara et al.

(10) Patent No.: US 12,176,071 B2
(45) Date of Patent: Dec. 24, 2024

(54) SYSTEMS AND METHODS FOR ULTRA-FAST IDENTIFICATION AND ABUNDANCE ESTIMATES OF MICROORGANISMS USING A KMER-DEPTH BASED APPROACH AND PRIVACY-PRESERVING PROTOCOLS

(71) Applicant: The Joan & Irwin Jacobs Technion-Cornell Institute, New York, NY (US)

(72) Inventors: Niamh B. O'Hara, Ridgewood, NY (US); Rachid Ounit, Riverside, CA (US)

(73) Assignee: The Joan & Irwin Jacobs Technion-Cornell Institute, New York, NY (US)

( * ) Notice: Subject to any disclaimer, the term of this patent is extended or adjusted under 35 U.S.C. 154(b) by 683 days.

(21) Appl. No.: 16/345,367

(22) PCT Filed: Oct. 26, 2016

(86) PCT No.: PCT/US2016/058862
§ 371 (c)(1),
(2) Date: Apr. 26, 2019

(87) PCT Pub. No.: WO2018/080477
PCT Pub. Date: May 3, 2018

(65) Prior Publication Data
US 2019/0318807 A1   Oct. 17, 2019

(51) Int. Cl.
*G16B 5/00* (2019.01)
*C12Q 1/6888* (2018.01)
(Continued)

(52) U.S. Cl.
CPC ........... *G16B 30/20* (2019.02); *C12Q 1/6888* (2013.01); *G16B 5/00* (2019.02); *G16B 30/00* (2019.02);
(Continued)

(58) Field of Classification Search
CPC .................................. G16B 5/00; G16B 50/00
See application file for complete search history.

(56) References Cited

U.S. PATENT DOCUMENTS

| | | | |
|---|---|---|---|
| 2013/0096943 A1 | 4/2013 | Carey et al. | |
| 2014/0136120 A1* | 5/2014 | Colwell | G16B 40/00 702/20 |
| 2015/0242565 A1* | 8/2015 | Li | G16B 30/20 702/27 |

FOREIGN PATENT DOCUMENTS

WO   WO-2016124600 A1 *  8/2016   ........... C12Q 1/6869

OTHER PUBLICATIONS

Rajendhran et al. Strategies for accessing soil metagenome for desired applications Biotechnology Advances vol. 26, pp. 576-590 (Year: 2008).*

(Continued)

*Primary Examiner* — Lori A. Clow
*Assistant Examiner* — Emilie A Neulen
(74) *Attorney, Agent, or Firm* — Mintz, Levin, Cohn, Ferris, Glovsky and Popeo, P.C.

(57) ABSTRACT

The present disclosure relates to the use of next generation technologies and analysis using a k-mer based approach which is depth-informed to classify microorganism and estimate abundance in single or mixed microorganismal populations in a rapid manner. The disclosure relates to methods for identifying taxa from environmentally or patient collected samples and processing these samples in a privacy-preserving manner.

22 Claims, 10 Drawing Sheets

(51) Int. Cl.
  G16B 30/00    (2019.01)
  G16B 30/10    (2019.01)
  G16B 30/20    (2019.01)
  G16B 50/00    (2019.01)
  G16B 50/10    (2019.01)
  G16B 50/30    (2019.01)
  G16B 50/40    (2019.01)
  G16B 50/50    (2019.01)

(52) U.S. Cl.
  CPC ............ *G16B 30/10* (2019.02); *G16B 50/00* (2019.02); *G16B 50/10* (2019.02); *G16B 50/30* (2019.02); *G16B 50/40* (2019.02); *G16B 50/50* (2019.02)

(56) References Cited

OTHER PUBLICATIONS

Petti Detection and Identification of Microorganisms by Gene Amplification and Sequencing Clinical Infectious Diseases vol. 44, pp. 1108-1114 (Year: 2007).*

Scholz et al. Improved Assemblies Using a Source-Agnostic Pipeline for MetaGenomic Assembly by Merging (MeGAMERGE) of Contigs Scientific Reports vol. 4 article 6480 (Year: 2014).*

Patel, J.B. 16S rRNA Gene Sequencing for Bacterial Pathogen Identification in the Clinical Laboratory. Molecular Diagnosis 6, 313-321 (2001). https://doi.org/10.1007/BF03262067 (Year: 2001).*

Franzosa, E.A., Huang, K., Meadow, J.F., Gevers, D., Lemon, K., Bohannan, B.J., Huttenhower, C., Identifying personal microbiomes using metagenomic codes. Proceedings of the National Academy of Sciences, 112(22): E2930-8, 2015.

Gymrek, M., McGuire, A.L., Golan, D., Halperin, E. and Erlich, Y., Identifying personal genomes by surname inference. Science, 339(6117), pp. 321-324, 2013.

Homer N, Szelinger S, Redman M, Duggan D, Tembe W, Muehling J, Pearson JU, Stephan DA, Nelson SF, Craig DW, Resolving individuals contributing trace amounts of DNA to highly complex mixtures using high-density SNP genotyping microarrays. PLOS Genet. Aug. 29, 2008; 4(8):e1000167.

Ounit, R., Wanamaker, S., Close, T.J., and Lonardi, S. Clark: fast and accurate classification of metagenomic and genomic sequences using discriminative k-mers. BMC genomics, 16(1):1, 2015.

Ounit, R., and Lonardi, S. Higher classification sensitivity of short metagenomic reads with clark-s. Bioinformatics, btw542, 2016.

J. I. Prosser, Dispersing misconceptions and identifying opportunities for the use of 'omics' in soil microbial ecology. Nature Reviews Microbiology, 13(7): 439-46, 2015.

Segata, N., Waldron, L., Ballarini, A., Narasimhan, V., Jousson, O., and Huttenhower, C .. Metagenomic microbial community profiling using unique clade-specific marker genes. Nature methods, 9(8), 811-814, 2012.

Sobih, A., Tomescu, A.I., Makinen, V., MetaFlow: Metagenomic profiling based on whole-genome coverage analysis with min-cost flows. bioRxiv, 2016.

International Search Report and Written Opinion mailed on Jan. 24, 2017 for International Application No. PCT/US2016/058862, filed Oct. 26, 2016.

Huang et al. (Feb. 2012) "ART:A Next-Generation Sequencing Read Simulator", Bioinformatics, 28(4):593-594.

Martiny et al. (Nov. 2011) "Functional Metagenomics Reveals Previously Unrecognized Diversity of Antibiotic Resistance Genes in Gulls", Frontiers in Microbiology, 2:1-11.

\* cited by examiner

SYSTEMS AND METHODS FOR ULTRA-FAST IDENTIFICATION AND ABUNDANCE ESTIMATES OF MICROORGANISMS USING A KMER-DEPTH BASED APPROACH AND PRIVACY-PRESERVING PROTOCOLS

CROSS-REFERENCE TO RELATED APPLICATION

This application is a national stage entry, filed under 35 U.S.C. § 371, of International Application No. PCT/US2016/058862, filed on Oct. 26, 2016, the contents of which are hereby fully incorporated by reference.

FIELD

The present disclosure relates to systems and methods for the identification of microorganisms and estimation of abundance in single or mixed-microorganismal samples using a novel approach using a depth-informed unique-marker based analysis to increase confidence in identification while keeping analysis speed high.

BACKGROUND

Hospital acquired infections are a common cause of morbidity and mortality in the United States. An estimated 30 billion in direct costs is spent on this problem. Unfortunately, environmental testing of microbes within the hospital is severely limited. Consequently, there is an urgent need for technology that can provide rapid and reliable identification of pathogens in the environment that may cause patient infections to direct intervention before patients get sick. Furthermore, there is pressing need for rapid identification of microorganisms in patient samples because early detection can be used to effectively guide treatment. Environmentally-versus patient-collected samples have very different profiles and warrant different technology to process in the laboratory and computationally.

Furthermore, patient privacy is of the utmost importance and is threatened in this age of genomic and metagenomics sequencing. There is a growing concern over the ability to protect personal genetic privacy (i.e., ancestry, ethnicity, probability to develop certain genetic disease). It has been found that the identities of people who participated anonymously in genetic research studies can be identified by cross-referencing the genomic data with publicly available information. Indeed, researchers have shown that even anonymized individuals can also easily be identified from their microbiome. While the protection of data privacy is a legal obligation in several countries (e.g., US privacy laws include COPPA, GINA, GLB, HIPPA and European laws include the European Union Data protection Directive), it is computationally challenging to build bioinformatics tools to address these needs. Accordingly, there is an urgent need to implement privacy protection as part of taxa classification software, a step that heretofore has been lacking.

SUMMARY

The present disclosure features methods for identification of microbes within the environment and patient samples. The present disclosure features methods of characterizing DNA sequence data by using lightweight data structures, sequence composition instead of sequence alignment, probabilistic models using a mixture of probabilistic distributions, and privacy-preserving protocols in the case intensive computations on the genomic data are outsourced.

In one aspect, the present disclosure provides for a method of identifying microorganisms, that includes: obtaining a sample including one or more microorganism populations; generating, by a control unit including a memory and a processor, genomic DNA sequence data for the one or more microorganism populations; determining, by the control unit, a set of k-mers of one or more genomic DNA regions from the one or more microorganism populations; comparing, by the control unit, the set of k-mers to a reference database; using an ultra-fast filtering process to remove sequenced reads that do not map unambiguously to one and only one organism without loss of identification performance or accuracy; determining, by the control unit, depth of sequence coverage of taxa specific sequences to identify one or more taxa from the one or more microorganism populations; modeling the frequency of k-mers in the sequenced sample that match the database using one or several probabilistic models per taxon; and modeling, by the control unit, the distribution of the frequency of the k-mers matching the database using one or more probabilistic models to estimate abundance of each identified one or more taxa.

In an embodiment, the method further comprises implementing a privacy-preserving scheme in a public server or cloud-based server without slowing down the taxa processing or analysis time. In an embodiment, the probabilistic model increases confidence while maximizing speed over other taxa identification methods.

In an embodiment, the set of k-mers includes at least 10 individual k-mers. In an embodiment, the set of k-mers includes at least 100 individual k-mers.

In an embodiment, the sample is obtained from a subject sample, or an environmental sample.

In an embodiment, the reference database may be subset to correspond to the sample source, whether patient or environmentally collected, to increase confidence while maximizing analysis speed. In an embodiment, the laboratory processing of samples may be tailored to the sample source, whether patient or environmentally collected, to optimize nucleotide extraction and downstream processing.

In an embodiment, the set of k-mers includes a plurality of k-mers each ranging from about 17 to about 63 nucleotides in length. In an embodiment, the set of k-mers includes a plurality of k-mers each ranging from about 17 to about 31 nucleotides in length. In an embodiment, the nucleic acids extracted and processed may be either DNA or RNA. In an embodiment, the nucleic acid sequence(s) of interest may be amplified prior to determining a k-mer set to use in analysis.

In another aspect, the present disclosure provides for a method of characterizing pathogenicity of one or more microorganism populations, that includes: obtaining a sample at a location including one or more microorganism populations at one or more time points; generating, by a control unit including a memory and a processor, genomic DNA sequence data for the one or more microorganism populations at each of the one or more time points; determining, by the control unit, a set of k-mers of one or more genomic DNA regions from the one or more microorganism populations; comparing, by the control unit, the set of k-mers to a reference database; determining, by the control unit, depth of coverage of taxa specific sequences to identify one or more taxa from the one or more microorganism populations; and modeling, by the control unit, the genomic DNA sequence data of the one or more genomic DNA regions data using one or more probabilistic models; generating, by the control unit, an abundance estimation of each identified one or more taxa; determining, based on the identified taxa, the pathogenicity of one or more microorganism populations; and implementing a protocol for eliminating microorganisms based on the pathogenicity assessment.

In an embodiment, the probabilistic model increases confidence while maximizing speed over other taxa identification methods. In an embodiment, the set of k-mers includes at least 10 individual k-mers. In an embodiment, the set of k-mers includes at least 100 individual k-mers. In an embodiment, the sample is obtained from a subject sample, an environmental sample, or a metadata and barcode sample. In an embodiment, the set of k-mers includes a plurality of k-mers each ranging from about 17 to about 63 nucleotides in length. In an embodiment, the set of k-mers includes a plurality of k-mers each ranging from about 17 to about 31 nucleotides in length.

In another aspect, the present disclosure provides for a tangible, non-transitory, computer-readable media having software encoded thereon, the software, when executed by a processor, operable to: receive genomic DNA sequence data for one or more microorganism populations from an obtained sample; determine a set of k-mers of one or more genomic DNA regions from the one or more microorganism populations; compare the set of k-mers to a reference database; determine depth of coverage of taxa specific sequences to identify one or more taxa from the one or more microorganism populations; and model the genomic DNA sequence data of the one or more genomic DNA regions data using one or more probabilistic models to estimate abundance of each identified one or more taxa.

In an embodiment, the sample is obtained from a subject sample, an environmental sample, or a metadata and barcode sample. In an embodiment, the set of k-mers includes at least 10 individual k-mers. In an embodiment, the set of k-mers includes a plurality of k-mers each ranging from about 17 to about 31 nucleotides in length.

Definitions

The new computational system outlined as described herein, "CLARICE" (from "clarus" in Latin meaning "bright", "clear"), uses an approach which includes i) a depth-informed analysis of sequence reads over regions of genomes unique to specific taxa (e.g., species, sub-species or strains) from an extensive set of reference sequences, ii) an accurate and ultra-fast technique to detect and analyze sequenced reads, iii) probabilistic models to predict the abundance estimation of each organism detected, and iv) a secure protocol to query and retrieve taxonomic information located in one or several outsourced database(s) containing genomic data.

Unless defined otherwise, all technical and scientific terms used herein have the meaning commonly understood by a person skilled in the art to which this disclosure belongs. The following references provide one of skill with a general definition of many of the terms used in this disclosure: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

By "alteration" is meant an increase or decrease. An alteration may be by as little as, for example, 1%, 2%, 3%, 4%, 5%, 10%, 20%, 30%, or by 40%, 50%, 60%, or even by as much as 75%, 80%, 90%, or 100%. An alteration may be a change in sequence relative to a reference sequence or sequence of sample collected at a different time point or a change in expression level, activity, or epigenetic marker.

By "ameliorate" is meant decrease, suppress, attenuate, diminish, arrest, or stabilize the development or progression of a disease.

By "biologic sample" is meant any tissue, cell, fluid, or other material derived from an organism or collected from the environment.

A taxon refers to a classification of a group of organisms of any rank including family, genus, species, subspecies, or strain.

In this disclosure, "comprises", "comprising", "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference condition.

"Detect" refers to identifying the presence, absence or amount of the pathogen or microorganism to be detected.

By "catalog" or "database" is meant the structured container or set of elements, in which elements can be, for example, reference sequences, k-mers, etc., that can be inserted, removed and searched automatically thanks to prebuilt functions (e.g., insertion/removal function or query function) available to the user. This container or set can be for example, an array, in which, each element can be stored by value (i.e., all bits contained in the element) or by reference (i.e., a key or address of the element in the computer memory).

By "database index" is meant an index or block of memory associated to a particular database or catalog that allows an efficient and fast query of an item within the database or an efficient and fast retrieval of all elements in the database.

By "diagnostic" is meant any method that identifies the presence of a pathologic condition or agent or characterizes the nature of a pathologic condition (e.g., an infection). Diagnostic methods differ in their sensitivity and specificity. While a particular diagnostic method may not provide a definitive diagnosis of a condition, it suffices if the method provides a positive indication that aids in diagnosis.

The phrase "in combination with" is intended to refer to all forms of administration that provide an agent, or the methods of the instant disclosure together with a second agent, such as an antiviral agent, or antibiotic agent, or an antifungal agent, where the two are administered concurrently or sequentially in any order.

The phrase "combination" embraces groups of compounds or non-drug therapies useful as part of a combination therapy. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject a single capsule having a fixed ratio of each therapeutic agent or in multiple, single capsules for each of the therapeutic agents.

The term "agent" as used herein is meant to refer to a polypeptide, polynucleotide, or fragment, or analog thereof, small molecule, inhibitory RNA, or other biologically active molecule.

By "disease" is meant any condition or disorder that damages or interferes with the normal function of a cell, tissue, or organ.

By "effective amount" is meant the amount required to ameliorate the symptoms of a disease (e.g., a neoplasia/tumor) relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fluorescent detection" is meant the measurement of the signal of a labeled moiety of at least one of the one or more nucleotides or nucleotide analogs. Sequencing using fluorescent nucleotides typically involves photobleaching the fluorescent label after detecting an added nucleotide. In some embodiments, fluorescent detection can include bead-based fluorescent, FRET, infrared labels, pyrophosphatase, ligase methods including labeled nucleotides or polymerase or use of cyclic reversible terminators. In some embodiments, fluorescent detection can include direct methods of nanopores or optical waveguide including immobilized single molecules or in solution. Photobleaching methods include a reduced signal intensity, which builds with each addition of a fluorescently labeled nucleotide to the primer strand. By reducing the signal intensity, longer DNA templates are optionally sequenced.

By "fragment" is meant a portion of a polypeptide or nucleic acid molecule. This portion contains, at least 1%, 5%, 10%, 20%, 30%, 40%, 50%, 60%, 70%, 80%, or 90% of the entire length of the reference nucleic acid molecule or polypeptide. A fragment may contain 5, 10, 20, 30, 40, 50, 60, 70, 80, 90, or 100, 200, 300, 400, 500, 600, 700, 800, 900, 1000 or more nucleotides or amino acids. In some embodiments, a fragment may contain less than 1% of the entire length of the reference nucleic acid molecule or polypeptide. A fragment may contain 150 base pairs (bps) of nucleic acid molecule.

A "kmer" or, "k-mer" (also called "lmer", "l-mer", "k-pattern" or "l-pattern") is a short sequence of DNA of k consecutive nucleotides (in the forward or reverse strand of the DNA molecule), where k (or l) is a natural integer higher than 1.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By "sensitivity" is meant the percentage of subjects with a particular disease that are correctly detected as having the disease. For example, an assay that detects 98/100 of infections has 98% sensitivity.

The phrase "nucleic acid" as used herein refers to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively. Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization will also vary in stringency. Wash stringency conditions can be defined by salt concentration and by temperature.

As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The term "gene" refers to a segment of deoxyribonucleic acid that encodes a polypeptide including the upstream and downstream regulatory sequences. Specifically, the term gene includes the promoter region upstream of the gene.

The term "promoter" or "promoter region" refers to a minimal sequence sufficient to direct transcription or to render promoter-dependent gene expression that is controllable for cell-type specific or tissue-specific gene expression, or is inducible by external signals or agents. Promoters may be located in the 5' or 3' regions of the gene. Promoter regions, in whole or in part, of a number of nucleic acids can be examined for sites of variation and/or mutation. In general, a promoter includes, at least, 50, 75, 100, 125, 150, 175, 200, 250, 300, 400, 500, 750, 1000, 1500, or 2000 nucleotides upstream of a given coding sequence (e.g., upstream of the coding sequence for genes). One of skill in the art will appreciate that a promoter location may vary outside these parameters for some genes, and also that some genes may comprise more than one promoter (e.g., multiple tissue specific promoters).

The term "sample" as used herein refers to any biological or chemical mixture for use in the method of the disclosure. The sample can be a biological sample. The sample can be collected from the surface of an environment (hospital, office building, building, shopping center, park, restaurant, plaza, mall, or public space) or individual.

By "marker" is meant any protein or polynucleotide having an alteration in expression level or activity that is associated with a disease or disorder. A marker may also mean a variant DNA or RNA sequence that has shown to contribute toward a disease or disorder.

By "mutation" is meant a DNA sequence found in the microbial sample that is not found in the corresponding DNA of that same microorganism in other samples. "Mutation" may also refer to patterns in the sequence of RNA from a sample that are not attributable to expected variations based on known information for an individual gene and are reasonably considered to be novel variations in, for example, the splicing pattern of one or more genes that has been specifically altered in the microbial cells of the sample.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$-COOH where n is 0-4, and the like. Similarly, pharmaceutically acceptable cations include, but are not limited to, sodium, potassium, calcium, aluminum, lithium and ammonium. Those of ordinary skill in the art will recognize further pharmaceutically acceptable salts for the pooled tumor specific neo-antigens provided herein, including those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "single-nucleotide polymorphism/simple nucleotide polymorphism" (or "SNP") is meant a variation in a single nucleotide which may occur at some specific position in the genome, where each variation is present to some degree within a population (e.g., >1%).

The term "subject" as used herein is meant to include vertebrates, preferably a mammal. Mammals include, but are not limited to, humans, camels, horses, goats, sheep, cows, dogs, cats, and the like.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used to indicate a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or a combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE FIGURES

FIG. 4A is a schematic of the CLARICE algorithm including the abundance estimations of organisms detected in a sample file. The main algorithm is described including details on how the abundance and relative abundances are predicted from the sequenced sample and database index of taxa specific and unique genomic markers (k-mers). This schematic describes the default setting in which CLARICE is run on a powerful server able to load into memory the database of taxa-specific and taxa-unique k-mers. FIG. 4B describes a variation of the schematic described in FIG. 4A. In this figure, it is assumed that the database of taxa-specific and taxa-unique k-mers is outsourced in a private/trusted server and CLARICE communicates with this server. FIG. 4C describes another variation of the schematic described in FIG. 4A. In this figure, it is assumed that the database of taxa-specific and taxa-unique k-mers is outsourced (fully or partially) in one or several untrusted servers and CLARICE communicates in a privacy-preserving manner with these servers.

DETAILED DESCRIPTION

Figure 1:
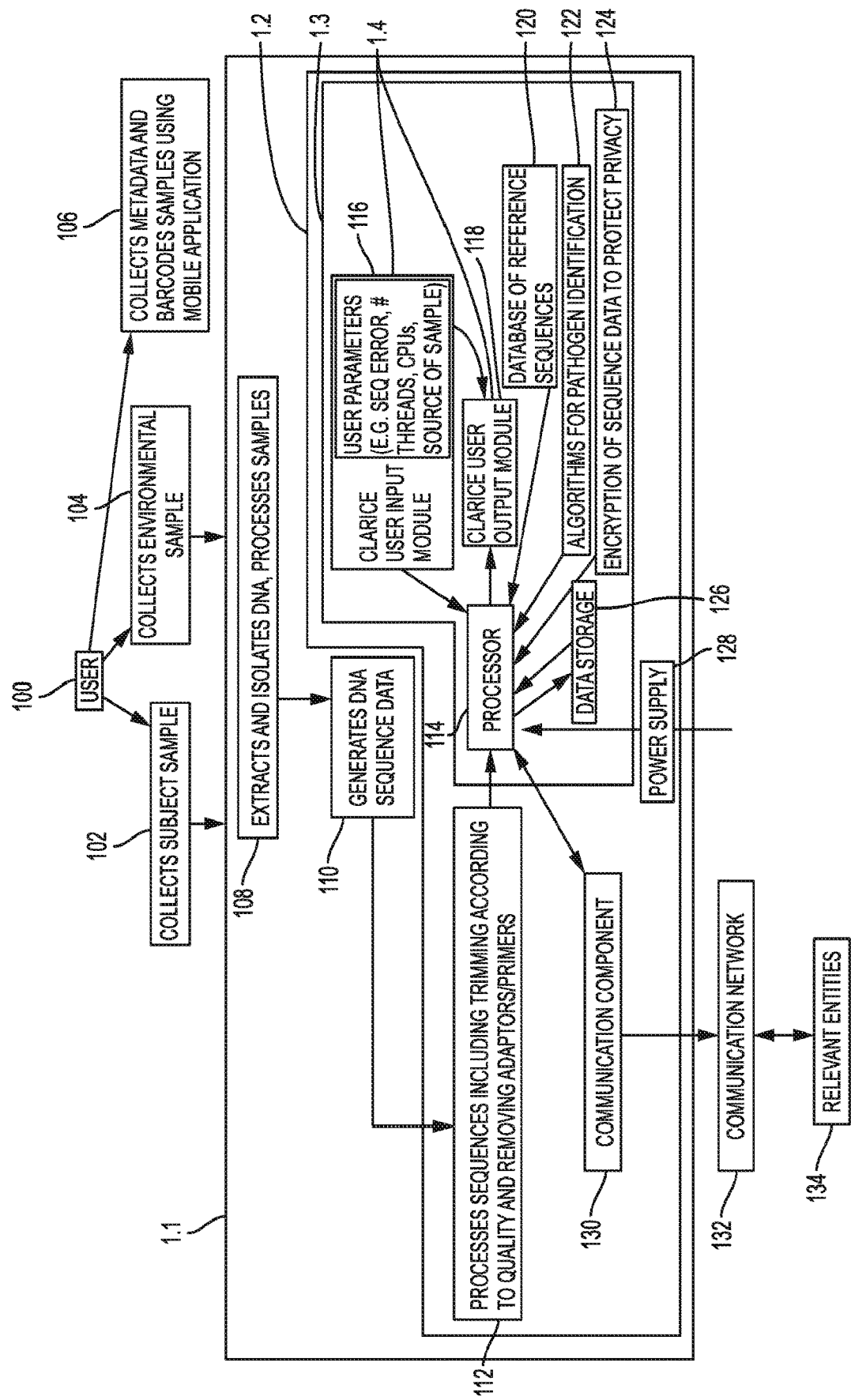
FIG. 1 is an illustration of the system which may be used for identification of microbes with potential embodiments as a device (1.1), a system (1.2), and/or a software (1.3).

The present disclosure features methods for identification of microbes within the environment and in patient samples. This disclosure is based, at least in part, on the discovery that by building a database to assess taxa specific and unique k-mers from thousands of taxa (e.g., species), combined with assessing sequence depth (or coverage) across these markers, it is possible to effectively and quickly identify all taxa present in single and mixed-microorganismal samples. More specifically, the present disclosure features methods of identification of taxa using a depth-informed approach in which the depth of sequence reads for up to hundreds of billions of specific and unique markers, built from a comprehensive database of all publicly available curated sequenced organisms (e.g., whole genome sequences from NCBI/RefSeq), is used to identify presence of a taxa. This approach is based on the concept that if a species/strain is present in a sample, one would expect to see an average minimum coverage across that species genome including across markers unique and specific to that species/strain. This disclosure is additionally based on the discovery that environmentally collected metagenomic samples are characteristically different from patient collected samples and warrant specific laboratory and computational processing (detailed below). Finally, this disclosure is based on the discovery that privacy-preserving schemes for these taxa-specific and unique k-mers can be performed quickly and efficiently and can be integrated into these novel systems and methods to protect patient privacy without slowing down the analysis time.

Current classification tools lack specificity and speed, two characteristics especially important in the field of medical diagnostics. Herein is proposed new systems and methods including a new algorithm and novel database construction that identifies taxa using an approach to increase confidence of identifying taxa while maximizing speed. According to the techniques here, a new computational system, "CLARICE" (from "clarus" in Latin meaning "bright", "clear"), uses an approach which includes i) a depth-informed analysis of sequence reads over regions of genomes unique to specific taxa (e.g. species, sub-species or strains) from an extensive set of reference sequences, ii) an accurate and ultra-fast technique to detect and analyze ambiguous sequenced reads, iii) probabilistic models to predict the abundance estimation of each organism detected, and iv) a secure protocol to query and retrieve taxonomic information located in one or several outsourced database(s) containing genomic data. Using a genome-wide coverage-informed approach allows one to side-step many of the problems associated with reliable identification of taxa using metagenomic samples (e.g., sequence similarity between different species, sequences that cannot be mapped unambiguously between several different species, etc.).

Specifically, the present disclosure facilitates movement from what has been termed "gene-centric" metagenomics, which involves analysis of individual genes that cannot be reliably tracked back to a source genome unless they are sequenced using a single-cell approach, to a "genome-centric" approach, which allows for more reliable identification of mixed-microorganismal samples (because it will not lead to misidentification due to horizontal gene transfer, mobile genetic elements, etc.), and downstream analysis including functional analysis [Prosser 2015]. Additionally, using a k-mer based approach allows one to drastically improve the speed of analysis. Two potential applications of this novel approach involve rapid identification of pathogens in environmental surveillance which may facilitate intervention and prevent transmission of pathogens, and rapid identification of pathogens involved in patient disease in order to guide treatment.

An additional weakness of current classifications tools is that they rarely recognize the source of the sample (e.g. environmentally collected versus patient sample) and are not optimized for different sources. Therefore, the same tool will be used for environmentally collected samples versus patient samples despite distinct differences in these samples. Clear distinction can even be found between the profiles of patient collected samples based on the area of the body from which the sample is collected (e.g. the skin profile is very different from the gut). Incorporating a priori knowledge of the sample source, as included herein, in both the laboratory processing of samples, such as using targeted methods to break open bacterial spores which are more often formed in the environment, and the computational methods results in more accurate and sensitive taxa classification.

Finally, current classification tools require demanding computational resources to run and these memory-intensive classification tools assume that they can trust the server or computational infrastructure in which they are installed and running. The cost to own and set up a private server and run these memory-intensive tools remains high. Lately, cheaper alternatives have been introduced, such as the cloud computing (e.g., cloud servers by Amazon, Google, Microsoft, etc.). CLARICE can take advantage of a cloud server and outsource the database of taxa-specific and unique k-mers as well as all memory-intensive computations. Indeed, by simply using a laptop (with a low memory architecture), a user can analyze a sequenced sample with CLARICE, which can perform the non-intensive computations on the laptop and delegate the memory intensive computations to the cloud. However, as soon as data are sent to the cloud it is difficult to guarantee that no suspicious activity would occur (data copy, data theft, data loss, data corruption, etc.) and that privacy would not be violated. Indeed, some cheap cloud servers are not private and may be untrusted (e.g., "Honest-but-curious" servers). Because it is possible to identify individuals from their personal genomic data and their microbial data [Gymrek et al, 2013, Homer et al, 2008, Franzosa et al. 2015], measures must be taken to protect the privacy of these sequence data whether samples are collected from patients or from the environment in which human DNA and individualized microbial signatures are found. Privacy protection of sequenced samples is especially important for samples collected in privacy sensitive areas, such as healthcare environments. There is no existing abundance estimation programs capable of analyzing environmental and/or clinical samples through a cloud server (trusted or untrusted) in a secure manner, without leaking private genomic information. However, the CLARICE system can work with cloud servers that are trusted or not—it can take into account the possibility that an outsourced server may be compromised (e.g. any data sent to it can be monitored, analyzed, copied, altered, etc.), but it can still preserve data privacy thanks to enhanced secure computing techniques. This program, CLARICE, is the first secure metagenome analysis program.

Laboratory culturing remains the gold standard to identify and characterize microbial populations in environmental and patient samples. Disadvantageously, this approach takes upwards of ~3 days (and in some cases as long as 2 weeks), depending on how slow-growing the microorganism is. Other disadvantages of laboratory culturing are that they are costly, and can only characterize microbes that can be cultured. There are also PCR based approaches available to classify taxa, but this approach again only allows for identification of a limited number of targeted taxa and provides limited data to characterize these taxa further (e.g. limitation on generating strain level data or characterization of populations including genetic diversity) and lacks specificity.

Recently, progress has been made in identification of microbes using next generation sequencing through comparison of metagenomic fragments to genomic databases, however, due to the complexity of biological systems and genome sequences, the current approaches are computationally demanding and time consuming Many of these approaches use an alignment-based approach which is especially time consuming. In addition, there is no standard method to quickly resolve ambiguous identification of sequences between two or more closely related or highly similar species. The "MetaFlow" program [Sobih et al, 2016] aims to estimate species abundance and relative abundance by taking into account ambiguous sequenced reads that can be equally mapped to different species/organisms. However, the MetaFlow can take hours to analyze a small/medium size sample (1 to 2 million short reads) because it relies on a sequence-alignment strategy (i.e., BLAST). So, the genome-wide depth-informed approach used in the MetaFlow program does not present a solution fast enough.

By using a k-mer based approach it is possible to reduce complexity in these systems to a computationally manageable problem, and drastically decrease the time it takes to classify taxa and estimate their abundance. Furthermore, combining a depth informed approach with this k-mer approach increases reliability in calling taxa, reducing false positives.

This novel system and methods has widespread application. For example, hospital acquired infections (HAIs) are a common cause of morbidity and mortality in the United States. One in 25 people who check into a hospital get an infection and 1 in 9 of these patients die from that infection. This makes hospital acquired infections a leading cause of death in the US and an estimated $30 billion in direct costs is spent on this problem. Studies have shown that hospitals can prevent between 20 and 70% of HAIs by modifying hospital practices, such as implementing cleaning practices that appropriately target pathogens. Even though, an increasing number of studies are showing that the hospital environment is acting as a significant reservoir for these pathogens, environmental testing is severely limited. This means that hospitals are cleaning blindly, and waiting until patients get sick to process samples and identify pathogens. This is because their current environmental testing tools, including ATP testing and culturing are slow, labor intensive, and costly. There is a pressing need for technology which can rapidly identify microbes in the environment.

Additionally, patients are widely monitored for incidence of antimicrobial resistant infection, but the environment is rarely monitored. Instead once patients get sick, samples are taken to be analyzed in different ways, such as by culturing and exposing to antimicrobials to determine if pathogens survive, or by amplification and sequencing of known antimicrobial associated loci. There is a great need to develop affordable, and rapid methods to characterize antimicrobial resistance from the environment, before patients get sick and to more accurately identify antimicrobial resistance in patient samples in a more rapid and specific manner.

A second important area of application involves rapid identification of taxa in patient samples. The time to diagnosis can be critical in guiding patient treatment and saving patient lives. It is common practice currently for doctors to collect a patient sample and then prescribe medication based on symptoms alone while they wait for days for lab results. This approach is problematic for a multitude of reasons. Firstly, the patient may not recover because they may be given the wrong treatment, which is especially worrisome in the event of an antimicrobial resistant infection. This approach also contributes to the alarming increase in antimicrobial resistance, which has reached the level of a global health crisis.

In addition to the hospital, there are many high risk environments in which this novel technology could be useful. For example, in the case of bio-terrorist attacks, food borne disease outbreaks, and epidemics, the ability to use nucleotide sequence data to reliably and rapidly identify microbial taxa could be of vital importance to those dealing in immigration, homeland security, food safety and infection control.

With the impressive ongoing advances in sequencing technology including the ability to rapidly and affordably sequence environmentally collected samples to a depth which allows for reliable identification of taxa, it is necessary to develop new culture independent technology.

Both within and outside the hospital setting, the environment is a major source of infections and antimicrobial resistance. In the context of epidemiology, understanding interactions between the human microbiome and other microbiomes in the environment is a major step to understand, cure and prevent propagation of infections. Indeed, about 60% of emerging infectious disease in humans are caused by zoonotic pathogens [e.g., West Nile virus, avian influenza, or Ebola; Jones et al., 2008]. The environment can not only provide the source of infectious disease, but it can also play a role in the development of antimicrobial resistance. Many known resistance genes did not initially appear in the clinical setting, but have their origins in the environment [Martinez, 2008; Allen et al., 2009], and the external environment hosts a large diversity of resistance genes, many of which have not yet been observed in human-associated bacteria [Martiny et al., 2011]. The importance in the role of the environment unscores the need for environmentally targeted technology which can rapidly and reliably classify taxa.

Hospital Acquired Infections

Hospital-acquired infection (HAI)—also known as nosocomial infection—is an infection that is contracted by a patient while they are under medical care. It can be spread in the hospital environment, nursing home environment, rehabilitation facility, clinic, or other clinical settings. Infection is spread to the susceptible patient in the clinical setting by a number of means. Health care staff can spread infection, in addition to contaminated equipment, surfaces, bed linens, or air droplets. The infection can originate from the outside environment, another infected patient, staff that may be infected, or in some cases, the source of the infection cannot be determined. In some cases, the microorganism originates from the patient's own microbiota, becoming opportunistic after surgery or other procedures that compromise the protective skin barrier or the immune system. Though the patient may have contracted the infection from their own body, the infection is still considered nosocomial since it develops in the health care setting.

In the United States, the Centers for Disease Control and Prevention estimated roughly 1.7 million hospital-associated infections, from all types of microorganisms, including bacteria and fungi combined, cause or contribute to 99,000 deaths each year. In Europe, where hospital surveys have been conducted, the category of gram-negative infections are estimated to account for two-thirds of the 25,000 deaths each year. Nosocomial infections can cause severe pneumonia and infections of the urinary tract, bloodstream and other parts of the body. Many types are difficult to treat with antimicrobials, and in addition, antimicrobial resistance can complicate treatment.

Species of interest known to be associated with HAIs include, but are not limited to viruses, prokaryotes and eukaryotes including *Clostridium difficile, Staphylococcus aureus* including Methicillin resistant strains (MRSA), *Klebsiella pneumoniae* and *K. oxytoca, Escherichia coli, Enterococcus* species including *E. faecalis* and *E. faecium* and Vancomycin-resistant Enteroccus (VRE), *Pseudomonas aeruginosa, Candida* species including *C. albicans, C. para-*

*psilosis*, and *C. glabrata*, *Streptococcus* species, Coagulase-negative *staphylococcus* species, *Enterobacter* species, *Acinetobacter baumannii*, *Proteus mirabilis*, Yeast species, *Stenotrophomonas maltophilia*, *Citrobacter* species, *Serratia* species, *Bacteroides* species, *Haemophilus* species, Viruses including adenovirus, herpes simplex virus, parainfluenza virus and norovirus, *Peptostreptococcus* species, additional *Klebsiella* species, additional *Clostridium* species, *Prevotella* species, *Morganella morganii*, *Lactobacillus* species, Legionnaire's disease. Additional species of interest include other taxa involved in global disease outbreaks including Avian influenza, swine influenza, Zika virus, West Nile virus, Ebola virus, *plasmodium* species, yellow fever virus, Dengue virus, Lassa virus, Human immunodeficiency virus, *Vibrio cholerae*, Middle East respiratory syndrome coronavirus (MERS-CoV), *Mycobacterium tuberculosis*, *Borrelia burgdorferi*, *Yersinia pestis*, viral hepatitis.

Micro-organisms are known to survive on inanimate 'touch' surfaces for extended periods of time. This can be especially troublesome in hospital environments where patients with immunodeficiencies are at enhanced risk for contracting nosocomial infections.

High touch surfaces commonly found in hospital rooms, such as bed rails, call buttons, touch plates, chairs, door handles, light switches, grab rails, intravenous poles, dispensers (alcohol gel, paper towel, soap), dressing trolleys, and counter and table tops are known to be contaminated with *Staphylococcus*, MRSA, VRE, and other nosocomial pathogens. For example, objects in closest proximity to patients have the highest levels of MRSA and VRE. This is why high touch surfaces in hospital rooms can serve as sources, or reservoirs, for the spread of pathogens to patients.

Infectious Disease

Infection is the invasion of an organism's body tissues by disease-causing agents, their multiplication, and the reaction of host tissues to these organisms and the toxins they produce. Infectious disease, also known as transmissible disease or communicable disease, is illness resulting from an infection. Infections are caused by infectious agents including viruses, viroids, prions, bacteria, nematodes such as parasitic roundworms and pinworms, arthropods such as ticks, mites, fleas, and lice, fungi such as ringworm, and other macroparasites such as tapeworms and other helminths. Hosts can fight infections using their immune system. Mammalian hosts react to infections with an innate response, often involving inflammation, followed by an adaptive response. Specific medications used to treat infections include a wide range of antimicrobials including antibiotics, antivirals, antifungals, antiprotozoals, and antihelminthics. Infectious diseases resulted in 9.2 million deaths in 2013 (about 17% of all deaths).

Among the vast varieties of microorganisms, relatively few cause disease in otherwise healthy individuals. Infectious disease results from the interplay between those few pathogens and the defenses of the hosts they infect. The appearance and severity of disease resulting from any pathogen, depends upon the ability of that pathogen to damage the host as well as the ability of the host to resist the pathogen. However, a host's immune system can also cause damage to the host itself in an attempt to control the infection. Clinicians therefore classify infectious microorganisms or microbes according to the status of host defenses—either as primary pathogens or as opportunistic pathogens:

Primary pathogens cause disease as a result of their presence or activity within the normal, healthy host, and their intrinsic virulence (the severity of the disease they cause) is, in part, a necessary consequence of their need to reproduce and spread. Many of the most common primary pathogens of humans only infect humans, however, many serious diseases are caused by organisms acquired from the environment or that infect non-human hosts.

Opportunistic pathogens can cause an infectious disease in a host with depressed resistance. Opportunistic infection may be caused by microbes ordinarily in contact with the host, such as pathogenic bacteria or fungi in the gastrointestinal or the upper respiratory tract, and they may also result from (otherwise innocuous) microbes acquired from other hosts (as in *Clostridium difficile* colitis) or from the environment as a result of traumatic introduction (as in surgical wound infections or compound fractures). An opportunistic disease requires impairment of host defenses, which may occur as a result of genetic defects (such as Chronic granulomatous disease), exposure to antimicrobial drugs or immunosuppressive chemicals (as might occur following poisoning or cancer chemotherapy), exposure to ionizing radiation, or as a result of an infectious disease with immunosuppressive activity (such as with measles, malaria or HIV disease). Primary pathogens may also cause more severe disease in a host with depressed resistance than would normally occur in an immune-sufficient host.

For infecting organisms to survive and repeat the infection cycle in other hosts, they (or their progeny) must leave an existing reservoir and cause infection elsewhere. Infection transmission can take place via many potential routes. Droplet contact, also known as the respiratory route, and the resultant infection can be termed airborne disease. If an infected person coughs or sneezes on another person the microorganisms, suspended in warm, moist droplets, may enter the body through the nose, mouth or eye surfaces. Fecal-oral transmission is defined by foodstuffs or water becoming contaminated (by people not washing their hands before preparing food, or untreated sewage being released into a drinking water supply) and the people who eat and drink them become infected. Common fecal-oral transmitted pathogens include *Vibrio cholerae*, *Giardia* species, rotaviruses, *Entameba histolytica*, *Escherichia coli*, and tape worms. Most of these pathogens cause gastroenteritis. Sexual transmission, with the resulting disease being called sexually transmitted disease, is another route. Oral transmission includes diseases that are transmitted primarily by oral means may be caught through direct oral contact such as kissing, or by indirect contact such as by sharing a drinking glass or a cigarette. Transmission may also be by direct contact. Some diseases that are transmissible by direct contact include athlete's foot, impetigo and warts. Vertical transmission requires direct contact from the mother to an embryo, fetus or baby during pregnancy or childbirth. It can occur when the mother gets an infection as an intercurrent disease in pregnancy. Iatrogenic transmission is due to medical procedures such as injection or transplantation of infected material.

Virulence

Virulence is the degree of pathogenicity within a group or species of parasites as indicated by case fatality rates and/or the ability of the organism to invade the tissues of the host. The pathogenicity of an organism—its ability to cause disease—is determined by its virulence factors. Virulence can describe either disease severity or a pathogen's infectivity.

In an ecological context, virulence can be defined as the host's parasite-induced loss of fitness. Virulence can be understood in terms of proximate causes—those specific traits of the pathogen that help make the host ill—and ultimate causes—the evolutionary pressures that lead to virulent traits occurring in a pathogen strain.

The ability of bacteria to cause disease is described in terms of the number of infecting bacteria, the route of entry into the body, the effects of host defense mechanisms, and intrinsic characteristics of the bacteria called virulence factors. Many virulence factors are so-called effector proteins that are injected into the host cells by special secretion machines such as the type 3 secretion system. Host-mediated pathogenesis is often important because the host can respond aggressively to infection with the result that host defense mechanisms do damage to host tissues while the infection is being countered.

The virulence factors of bacteria are typically proteins or other molecules that are synthesized by enzymes. These proteins are coded for by genes in chromosomal DNA, bacteriophage DNA or plasmids. Certain bacteria employ mobile genetic elements and horizontal gene transfer. Therefore, strategies to combat certain bacterial infections by targeting these specific virulence factors and mobile genetic elements have been proposed. Bacteria use quorum sensing to synchronize release of the molecules. These are all proximate causes of morbidity in the host.

Pathogenicity

In biology, a pathogen in the oldest and broadest sense is anything that can produce disease, a term which came into use in the 1880s. Typically the term is used to describe an infectious agent such as a virus, bacterium, prion, fungus, viroid, or parasite that causes disease in its host. The host may be a human, an animal, a plant, a fungus, or even another micro-organism.

There are several substrates including pathways where the pathogens can invade a host. The principal pathways have different episodic time frames, but soil contamination has the longest or most persistent potential for harboring a pathogen. Diseases caused by organisms in humans are known as pathogenic diseases.

Pathogenicity is the potential disease-causing capacity of pathogens. Pathogenicity is related to virulence in meaning, but some authorities have come to distinguish it as a qualitative term, whereas the latter is quantitative. By this standard, an organism may be said to be pathogenic or non-pathogenic in a particular context, but not "more pathogenic" than another. Such comparisons are described instead in terms of relative virulence. Pathogenicity is also distinct from the transmissibility of the virus, which quantifies the risk of infection. A pathogen may be described in terms of its ability to produce toxins, enter tissue, colonize, hijack nutrients, and its ability to immunosuppress the host.

Sequencing Methods

In some embodiments, the present disclosure is based on employing one or more sequencing methods to characterize micro-organismal populations and determine their viability and risk of causing infection. A number of sequencing technologies, such as Next Generation Sequencing, may be used.

Multiple, fragmented sequence reads must be assembled together on the basis of their overlapping areas. Next-generation sequencing applies to genome sequencing, genome resequencing, transcriptome profiling (RNA-Seq), DNA-protein interactions (ChIP-sequencing), and epigenome characterization. Resequencing is necessary, because the genome of a single individual of a species will not indicate all of the genome variations among other individuals of the same species. The high demand for low-cost sequencing has driven the development of high-throughput sequencing (or next-generation sequencing) technologies that parallelize the sequencing process, producing thousands or millions of sequences concurrently. High-throughput sequencing technologies are intended to lower the cost of DNA sequencing beyond what is possible with standard dye-terminator methods. In ultra-high-throughput sequencing as many as 500,000 sequencing-by-synthesis operations may be run in parallel.

The first of the next-generation sequencing technologies, massively parallel signature sequencing (or MPSS), is a bead-based method that uses a complex approach of adapter ligation followed by adapter decoding, reading the sequence in increments of four nucleotides. This method makes it susceptible to sequence-specific bias or loss of specific sequences. The essential properties of the MPSS output are typical of later "next-generation" data types, including hundreds of thousands of short DNA sequences. In the case of MPSS, these are typically used for sequencing cDNA for measurements of gene expression levels.

The Polony sequencing method was among the first next-generation sequencing systems and was used to sequence a full E. coli genome in 2005. It combined an in vitro paired-tag library with emulsion PCR, an automated microscope, and ligation-based sequencing chemistry to sequence an E. coli genome at an accuracy of >99.9999% and a cost approximately 1/9 that of Sanger sequencing.

The 454 pyrosequencing method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence read-outs.

Illumina (Solexa) sequencing involves a sequencing method based on reversible dye-terminators technology, and engineered polymerases. It is based on "DNA Clusters" or "DNA colonies", which involves the clonal amplification of DNA on a surface. In this method, DNA molecules and primers are first attached on a slide or flow cell and amplified with polymerase so that local clonal DNA colonies, later coined "DNA clusters", are formed. To determine the sequence, four types of reversible terminator bases (RT-bases) are added and non-incorporated nucleotides are washed away. A camera takes images of the fluorescently labeled nucleotides. Then the dye, along with the terminal 3' blocker, is chemically removed from the DNA, allowing for the next cycle to begin. Unlike pyrosequencing, the DNA chains are extended one nucleotide at a time and image acquisition can be performed at a delayed moment, allowing for very large arrays of DNA colonies to be captured by sequential images taken from a single camera.

Decoupling the enzymatic reaction and the image capture allows for optimal throughput and theoretically unlimited sequencing capacity. With an optimal configuration, the ultimately reachable instrument throughput is thus dictated solely by the analog-to-digital conversion rate of the camera, multiplied by the number of cameras and divided by the number of pixels per DNA colony required for visualizing them optimally (approximately 10 pixels/colony). In 2012, with cameras operating at more than 10 MHz A/D conversion rates and available optics, fluidics and enzymatics, throughput can be multiples of 1 million nucleotides/second, corresponding roughly to 1 human genome equivalent at 1× coverage per hour per instrument, and 1 human genome re-sequenced (at approx. 30×) per day per instrument (equipped with a single camera).

SOLiD sequencing technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Illumina sequencing. This sequencing by ligation method has been reported to have some issue sequencing palindromic sequences.

Ion semiconductor sequencing uses standard sequencing chemistry, but with a novel, semiconductor based detection system. This method of sequencing is based on the detection of hydrogen ions that are released during the polymerisation of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

DNA nanoball sequencing is a type of high throughput sequencing technology used to determine the entire genomic sequence of an organism. The company Complete Genomics uses this technology to sequence samples submitted by independent researchers. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run and at low reagent costs compared to other next generation sequencing platforms. However, only short sequences of DNA are determined from each DNA nanoball which makes mapping the short reads to a reference genome difficult. This technology has been used for multiple genome sequencing projects and is scheduled to be used for more.

Heliscope sequencing is a method of single-molecule sequencing that uses DNA fragments with added poly-A tail adapters which are attached to the flow cell surface. The next steps involve extension-based sequencing with cyclic washes of the flow cell with fluorescently labeled nucleotides (one nucleotide type at a time, as with the Sanger method). The reads are performed by the Heliscope sequencer. The reads are short, averaging 35 bp.

Single molecule real time sequencing (SMRT sequencing) is based on the sequencing by synthesis approach. The DNA is synthesized in zero-mode wave-guides (ZMWs)—small well-like containers with the capturing tools located at the bottom of the well. The sequencing is performed with use of unmodified polymerase (attached to the ZMW bottom) and fluorescently labelled nucleotides flowing freely in the solution. The wells are constructed in a way that only the fluorescence occurring by the bottom of the well is detected. The fluorescent label is detached from the nucleotide upon its incorporation into the DNA strand, leaving an unmodified DNA strand. According to Pacific Biosciences (PacBio), the SMRT technology developer, this methodology allows detection of nucleotide modifications (such as cytosine methylation). This happens through the observation of polymerase kinetics. This approach allows reads of 20,000 nucleotides or more, with average read lengths of 5 kilobases. In 2015, Pacific Biosciences announced the launch of a new sequencing instrument called the Sequel System, with 1 million ZMWs compared to 150,000 ZMWs in the PacBio RS II instrument.

DNA sequencing methods currently under development include reading the sequence as a DNA strand transits through nanopores, and microscopy-based techniques, such as atomic force microscopy or transmission electron microscopy that are used to identify the positions of individual nucleotides within long DNA fragments (>5,000 bp) by nucleotide labeling with heavier elements (e.g., halogens) for visual detection and recording. Third generation technologies aim to increase throughput and decrease the time to result and cost by eliminating the need for excessive reagents and harnessing the processivity of DNA polymerase.

Nanopore sequencing is based on the readout of electrical signals occurring at nucleotides passing by alpha-hemolysin pores covalently bound with cyclodextrin. The DNA passing through the nanopore changes its ion current. This change is dependent on the shape, size and length of the DNA sequence. Each type of the nucleotide blocks the ion flow through the pore for a different period of time. The method has a potential of development as it does not require modified nucleotides, however single nucleotide resolution is not yet available.

Two main areas of nanopore sequencing in development are solid state nanopore sequencing, and protein based nanopore sequencing. Protein nanopore sequencing utilizes membrane protein complexes ∝-Hemolysin and MspA (Mycobacterium Smegmatis Porin A), which show great promise given their ability to distinguish between individual and groups of nucleotides. In contrast, solid-state nanopore sequencing utilizes synthetic materials such as silicon nitride and aluminum oxide and it is preferred for its superior mechanical ability and thermal and chemical stability. The fabrication method is essential for this type of sequencing given that the nanopore array can contain hundreds of pores with diameters smaller than eight nanometers.

The concept originated from the idea that single stranded DNA or RNA molecules can be electrophoretically driven in a strict linear sequence through a biological pore that can be less than eight nanometers, and can be detected given that the molecules release an ionic current while moving through the pore. The pore contains a detection region capable of recognizing different bases, with each base generating various time specific signals corresponding to the sequence of bases as they cross the pore which are then evaluated. When implementing this process it is important to note that precise control over the DNA transport through the pore is crucial for success. Various enzymes such as exonucleases and polymerases have been used to moderate this process by positioning them near the pore's entrance.

Another approach uses measurements of the electrical tunneling currents across single-strand DNA as it moves through a channel. Depending on its electronic structure, each base affects the tunneling current differently, allowing differentiation between different bases. The use of tunneling currents has the potential to sequence orders of magnitude faster than ionic current methods and the sequencing of several DNA oligomers and micro-RNA has already been achieved.

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identify its sequence in the DNA being sequenced.

This method of sequencing utilizes binding characteristics of a library of short single stranded DNA molecules (oligonucleotides), also called DNA probes, to reconstruct a target DNA sequence. Non-specific hybrids are removed by washing and the target DNA is eluted. Hybrids are re-arranged such that the DNA sequence can be reconstructed. The benefit of this sequencing type is its ability to capture a large number of targets with a homogenous coverage. A large number of chemicals and starting DNA is usually required. However, with the advent of solution-based hybridization, much less equipment and chemicals are necessary.

Mass spectrometry may be used to determine DNA sequences. Matrix-assisted laser desorption ionization time-of-flight mass spectrometry, or MALDI-TOF MS, has specifically been investigated as an alternative method to gel electrophoresis for visualizing DNA fragments. With this method, DNA fragments generated by chain-termination sequencing reactions are compared by mass rather than by size. The mass of each nucleotide is different from the others and this difference is detectable by mass spectrometry. Single-nucleotide mutations in a fragment can be more easily detected with MS than by gel electrophoresis alone. MALDI-TOF MS can more easily detect differences between RNA fragments, so researchers may indirectly sequence DNA with MS-based methods by converting it to RNA first.

The higher resolution of DNA fragments permitted by MS-based methods is of special interest to researchers in forensic science, as they may wish to find single-nucleotide polymorphisms in human DNA samples to identify individuals. These samples may be highly degraded so forensic researchers often prefer mitochondrial DNA for its higher stability and applications for lineage studies. MS-based sequencing methods have been used to compare the sequences of human mitochondrial DNA from samples in a Federal Bureau of Investigation database and from bones found in mass graves of World War I soldiers.

Early chain-termination and TOF MS methods demonstrated read lengths of up to 100 base pairs. Researchers have been unable to exceed this average read size; like chain-termination sequencing alone, MS-based DNA sequencing may not be suitable for large de novo sequencing projects. Even so, a recent study did use the short sequence reads and mass spectroscopy to compare single-nucleotide polymorphisms in pathogenic Streptococcus strains.

In microfluidic Sanger sequencing the entire thermocycling amplification of DNA fragments as well as their separation by electrophoresis is done on a single glass wafer (approximately 10 cm in diameter) thus reducing the reagent usage as well as cost. In some instances researchers have shown that they can increase the throughput of conventional sequencing through the use of microchips. Research will still need to be done in order to make this use of technology effective.

Transmission electron microscopy DNA sequencing directly visualizes the sequence of DNA molecules using electron microscopy. The first identification of DNA base pairs within intact DNA molecules by enzymatically incorporating modified bases, which contain atoms of increased atomic number, direct visualization and identification of individually labeled bases within a synthetic 3,272 base-pair DNA molecule and a 7,249 base-pair viral genome has been demonstrated.

The RNAP sequencing method is based on use of RNA polymerase (RNAP), which is attached to a polystyrene bead. One end of DNA to be sequenced is attached to another bead, with both beads being placed in optical traps. RNAP motion during transcription brings the beads in closer and their relative distance changes, which can then be recorded at a single nucleotide resolution. The sequence is deduced based on the four readouts with lowered concentrations of each of the four nucleotide types, similarly to the Sanger method. A comparison is made between regions and sequence information is deduced by comparing the known sequence regions to the unknown sequence regions.

Methods have been developed to analyze full sets of protein interactions using a combination of 454 pyrosequencing and an in vitro virus mRNA display method. Specifically, this method covalently links proteins of interest to the mRNAs encoding them, then detects the mRNA pieces using reverse transcription PCRs. The mRNA may then be amplified and sequenced. The combined method was titled In Vitro Virus High Throughput Sequencing (IVV-HiTSeq) and can be performed under cell-free conditions, though its results may not be representative of in vivo conditions.

The success of a DNA sequencing protocol is dependent on the sample preparation. A successful DNA extraction will yield a sample with long, non-degraded strands of DNA which require further preparation according to the sequencing technology to be used. For Sanger sequencing, either cloning procedures or PCR are required prior to sequencing. In the case of next generation sequencing methods, library preparation is required before processing.

With the advent of next generation sequencing, Illumina and Roche 454 methods have become a common approach to transcriptomic studies (RNAseq). RNA can be extracted from tissues of interest and converted to complimentary DNA (cDNA) using reverse transcriptase—a DNA polymerase that synthesizes a complimentary DNA based on existing strands of RNA in a PCR-like manner Complimentary DNA can be processed the same way as genomic DNA, allowing the expression levels of RNAs to be determined for the tissue selected.

Sample Collection Module

Sample collection may be conducted using commercially available kits, published methods, or novel technology. Samples collected are labeled and added to a database of collected specimens using a mobile app (iOS and Android) we have developed for collection in hospitals, including time-stamped images of sample labels, the room number, and the location swabbed. These are included to decrease human error and facilitate streamlined sample collection. Targeted methods are used to collect samples from the environment versus from patient samples such as protocol changes including changes to duration of swabbing, method of collection, swab or collection vessel used, and alteration of buffers used to preserve sample for downstream processing.

Additionally, the methods of the disclosure are ideally suited for the preparation of kits. This disclosure features kits for identifying the viability of detected micro-organisms based upon certain gene characteristics, gene specific primers for use in polymerase chain reaction (PCR), and instructions for use. The disclosure also features kits for detecting the risk of a micro-organism causing infection. These kits may be used to process patient samples or samples collected from the environment. Environmentally targeted kits may include swabs which are optimized for maximum collection of sample off of surfaces, as well as release of said sample into buffer to facilitate downstream applications including extractions and purification of DNA, or RNA. Buffers may also be optimized to neutralize cleaning materials often found on hospital surfaces so these cleaning materials don't degrade the sample or interfere in downstream processes including extraction, purification, preparation for sequencing and sequencing. Environmentally targeted kits may also include a permanent UV marker and UV light to facilitate collection of sample at the same location at multiple time points. Additional tools may also be included in the kit to aid in sample collection and tracking including a mobile app which has augmented reality capabilities to mark sample collection locations.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the disclosure, and, as such, may be considered in making and practicing the disclosure. Particularly useful techniques for particular embodiments will be discussed in the sections that follow.

Sample Processing and Sequencing Module

Sample processing may follow well-established published protocols including commercially available kits for DNA extraction and purification, and Qubit 2.0 fluorimeter quantification. Library prep may be conducted following established published protocols known to those of skill in the art. Additional laboratory steps may be added appropriately to tailor the protocol to process samples collected from the environment versus patient samples. Specifically, steps may be added to break open tougher fungal and bacterial spores which characteristically form in certain environments. Steps may include, but are not limited to, a freeze thaw step, using a bead beater, and/or using targeted enzymes.

Samples may be sequenced using available next generation sequencing technology as outlined in the sequencing definitions section. For example, in one illustrative embodiment, paired end (125×125) sequencing may be conducted using an Illumina HiSeq 2500 machine.

Sequence Processing Module

Sequences may then be trimmed for quality bases using available bioinformatics tools or custom scripts based on a Q20 cutoff and sequencing adaptors may be trimmed using custom scripts and/or available tools.

Database Module

The database creation and abundance estimation algorithm are described in FIGS. 3 to 6. The database creation may include a filtering process by removing sequence data from over-represented taxa in order to alleviate the computational processing. During the database creation or after the database creation, the database files may also be transformed to a probabilistic data-structure, such as a set of Bloom filters. In such a case, a Bloom filter may be defined to represent at most one taxa (e.g. variable "T"), and the elements of the Bloom-filter are the T-specific/unique k-mers.

Figure 3:
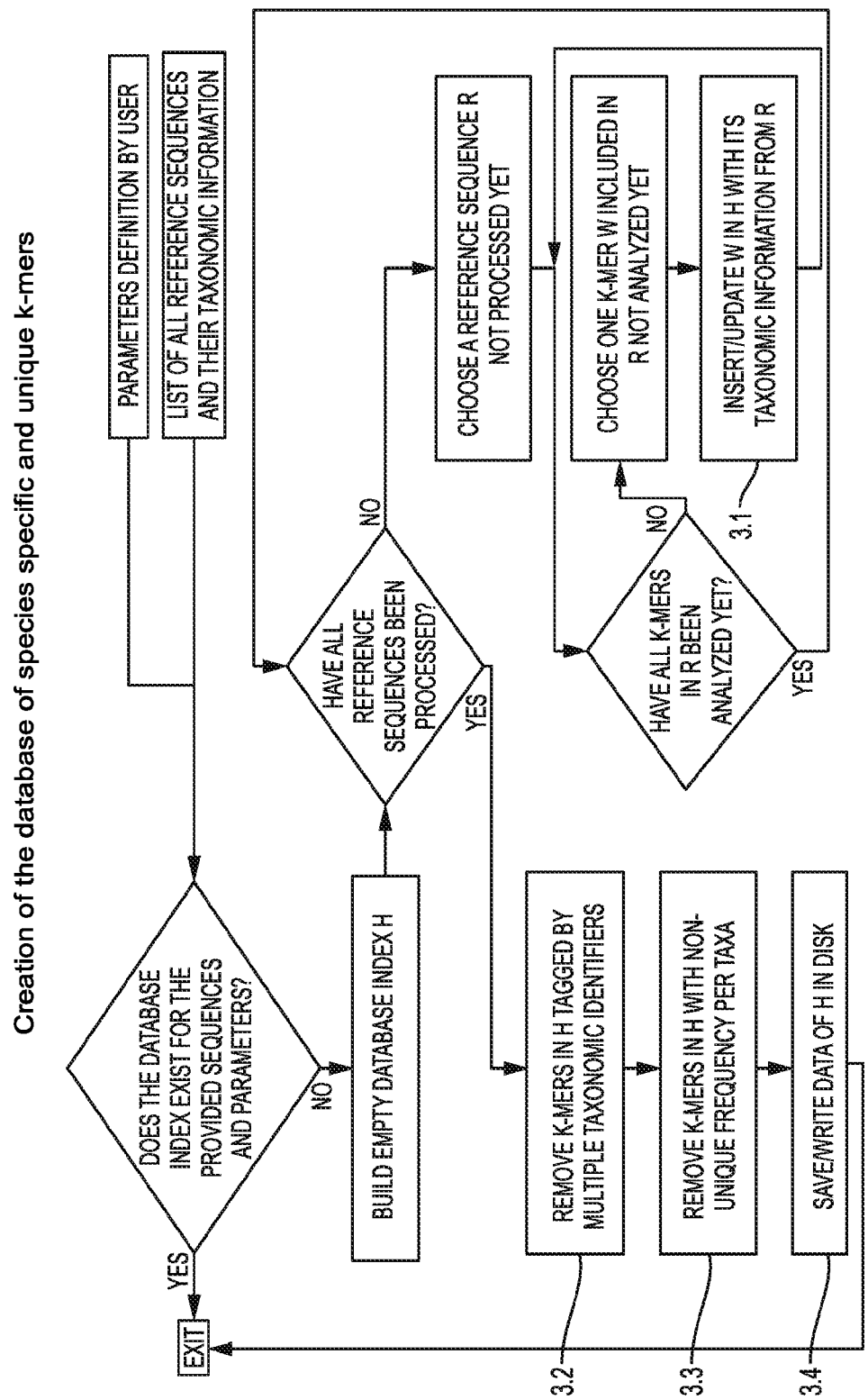
FIG. 3 is a schematic of how the database of taxa specific and unique genomic markers (i.e., k-mers) is built for a provided k value and a list of reference sequences with their taxonomic information.

The algorithm to create the database may contain some variations from the description of the algorithm provided for FIG. 3. For example, the user may select a tailored database for specific environment type, microbial habitats, or source of sample (environmentally collected versus patient sample). In such a case, some samples may be analyzed with a database defined with only bacterial sequences; some other samples may be analyzed with bacterial, virusal and fungal sequences etc. Another example of variation for the database creation is in the methods used to estimate similarity between k-mers. By default, exact matching is required to consider whether two k-mers are identical but the creation may also use partial matching instead of exact matching, for example, using the edit-distance, Hamming distance, Euclidean distance, or any norm defined on a vector space.

Figure 6:
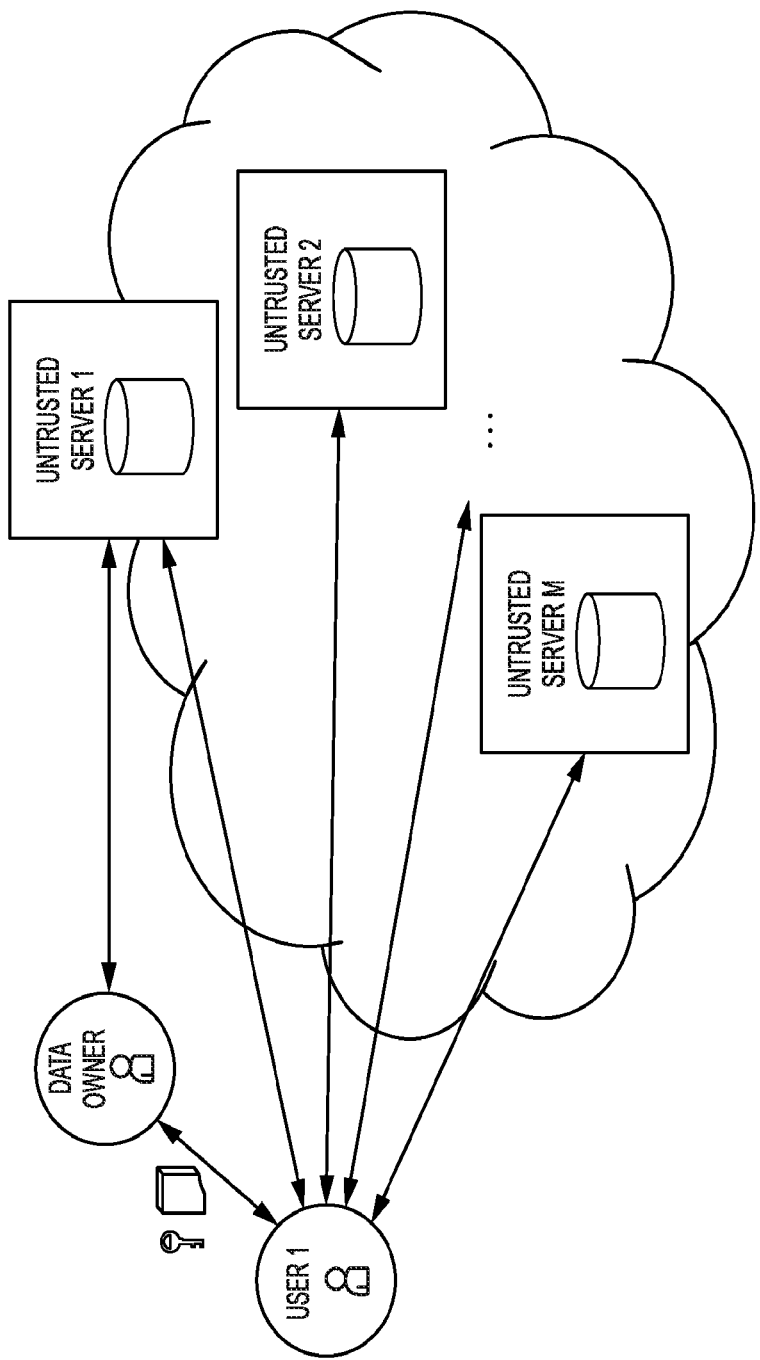
FIG. 6 describes a flow chart for the process of setting up the database by a data owner on one or several servers potentially untrusted and the communication between one user with the aforementioned server(s).

In FIG. 6, the data owner sets up one or several servers that are potentially untrusted and uses them to store taxonomic information (e.g., the database of taxa-specific and taxa-unique k-mers). However, the data owner assumes that these servers are indeed untrusted and thus, using a set of cryptographic techniques and a set of secret parameters and keys, he/she creates and stores in these servers an encrypted database of taxa-specific and taxa-unique k-mers in such a manner that only he/she and any authorized user with knowledge of the cryptographic techniques used for encryption and the set of secret parameters and keys can decipher the stored information. This encrypted database of taxa-specific and taxa-unique k-mers can be built using one or several of the encryption techniques described and mentioned in the section entitled "Security protocols and privacy-preserving techniques". In order to build an encrypted database, the data owner may run first the algorithm of the database described in FIG. 3 and then may encrypt taxa-specific and taxa-unique k-mers using one or several cryptographic functions using a set of secret parameters and keys that only the data owner holds and knows. In order to authorize any legitimate user to query information from an encrypted database stored in any of these servers, the data owner provides to this user, through a secure communication channel, a copy of the secrete parameters and keys so the user may query and decipher taxonomic information.

Analysis Module

This disclosure refers to the characterization of either single or mixed-microorganismal samples collected, and may include culturing mixed-microorganismal samples before sequencing in order to isolate a single species but mostly involves culture-independent analysis. These systems and computational methods include using a sliding window analysis over sequence reads to match to a catalog or a database of taxa-specific markers (i.e., a marker or k-mer is specific to a species S if it appears only in any reference sequence of S and does not appear without mismatches in any reference sequence from other species than S) and taxa-unique (i.e., a k-mer or genomic marker is species-unique if it does appear in the species S only once and so is repeated identically only with mismatches) with a count of reads that match each taxa-specific and taxa-unique kmers to determine depth of reads across taxon genome. This method may include analyzing metagenomics sequence data collected from the environment or from patient samples and the database may be tailored to include sequences of organisms that are typically found in said source (e.g.

species specific to certain environments or body locations for patient samples) as well as all closely related organisms. This method can also include a pre-analysis of each sequenced read in order to determine if the read can be mapped to multiple regions across multiple species without the same alignment/mapping quality (such a situation is called an "ambiguous read"). This method may also include the removal of ambiguous reads in order to reduce the computational burden and complexity of the abundance estimations as well as to speed up the taxa depth/coverage estimations. This method could be useful in many applications, such as in hospitals where such technology could allow hospitals to appropriately adjust cleaning approaches in an informed manner, and could help guide additional prevention strategies and/or empiric antimicrobial therapy.

While methods exist for identification of microbes from single and mixed-microbial populations, the present disclosure outlines an approach to combine a k-mer based approach with a sequence depth based approach in order to reliably estimate the abundance of all taxa present with ultra-high computational speed. Methods described may identify taxa by comparing the k-mers in each sequence read against the catalog of species-unique and species-specific k-mers and consider only read assignments that are unambiguous (e.g., a read R is unambiguously assigned to a taxon/species T if it is impossible to assign R to another taxon/species than T with the same mapping quality or assignment quality).

More specifically, for microorganisms in a sample for which there is sufficient sequence coverage and sequence uniqueness to differentiate from other microbes, the method to identify taxa may involve a sliding windowed analysis in which sequence reads are compared to a kmer database including taxa unique loci. Minimal sequence depth will be calculated by counting the number of k-mers which match taxa specific kmers to estimate depth for a taxa. This minimum sequence depth for the taxa S is estimated by analyzing the distribution of the count of all k-mers unique and specific to S. In the case of high quality reads, the distribution of this k-mers count is expected to be a Poisson distribution of parameter the minimum sequence depth, which corresponds to the k-mers count of maximum probability. However, bias due to sequencing errors or sequences from unknown and closely related taxa can interfere and alter the expected Poisson distribution. In such a situation, the k-mers count is mixture of Poisson distributions or a Gamma-Poisson mixture. A minimum threshold will need to be met of about 0.2% of k-mers belonging to a specific taxa from the total number of taxa-specific and taxa-unique k-mers identified in the sample before a taxa is identified as present in a sample in order to reliably identify said taxa.

These calculations may be computed on individual microbes or pooled populations of microbes (as found in metagenomic samples) and different algorithms may be used to calculate these alternative sample types. These methods may involve using sequence data analyzed using a processor and memory by using computer instructions to execute specific analyses.

For microorganisms in a sample which are able to be identified down to the subspecies level or which are identified to species level for species that are widely known to be pathogenic, comparisons may be made to a database which includes pathogenicity data to characterize the nature of microbes in said sample.

Sequence data referred to in this disclosure may include, but is not limited to, RNA, DNA and protein sequence from a number of different organisms including fungi, bacteria, viruses, viroids, and parasites.

This disclosure may have many applications. For example, it may illuminate the microbial ecosystems on hospital surfaces and alert them to the presence of pathogens, and that have a high risk of infecting patients. This information will allow hospitals to clean in a more informed manner, using cleaning tools suited to the pathogens present. It also alerts the hospital to the presence of pathogens before patients get sick, driving intervention to decrease the risk to patients.

This disclosure may also characterize antimicrobial resistance in microbial populations. This may involve identifying antimicrobial resistance loci based on a database.

An additional potential embodiment of this disclosure is the comparison of sequences and markers to determine relatedness to microorganisms found in other local and distant areas, which could indicate avenues of transmission and spread of these pathogens and antimicrobial resistance. This information may be applied in many scenarios, for example to pinpoint and control the source of an outbreak.

This disclosure is an improvement on current classification tools because it is rapid (on average it is 2-3 times faster than the standard and popular MetaPhlAn [Segata et al, 2012], significantly more accurate (on average the accuracy is significantly increased by one order of magnitude compared to the MetaPhlAn's accuracy), flexible/modulable (the user can focus the analysis on species of interest, e.g., a list of pathogens provided in input of the program), and effective (e.g., it will be able to characterize microbes that can't be cultured).

It is understood that one or more of the below methods, or aspects thereof, may be executed by at least one control unit. The term "control unit" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the control unit in conjunction with one or more other components, as would be appreciated by a person of ordinary skill in the art.

Furthermore, the control unit of the present disclosure may be embodied as non-transitory computer readable media containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed throughout a computer network so that the program instructions are stored and executed in a distributed fashion, e.g., by a telematics server or a Controller Area Network (CAN).

Preferred Embodiments with Reference to Figures

Included is the description of the embodiments of the systems and methods for identification of taxa using sequence data. These systems and methods are described in more detail here and in reference to the figures.

FIG. 1 is a schematic block diagram of an exemplary embodiment of the system disclosed including a sequencing device (1.1), a system (1.2), and/or a software (1.3). The device may be portable or set up on site to rapidly characterize microbial populations in a subject sample or in the environment. Alternatively, the system may receive sequence data which the user 100 collects from the subject 102, and/or the environment 104, and/or metadata (e.g., barcode samples) 106, followed by DNA extraction and processing 108, generation of sequence data 110, and computational processing of generated sequences 112, which may be parsed to processor 114. According to the techniques herein, the system may include the capability of processing the sequence data using commercially available sequence cleaning tools or custom scripts including the ability to trim out poor quality reads, remove adapter sequences, followed by (1.3) use of a novel k-mer-depth based approach, CLARICE, for identification of microbes to the species or subspecies level. These methods including CLARICE may be packaged as a software, to quickly and reliably identify taxa. The disclosed methods include classifying taxa (1.4) using CLARICE which in addition to using a sequence depth informed, k-mer based approach, uses a similarity based algorithm to utilize a database of reference sequences 120 to reliably and quickly identify microorganisms. Processor 114 may accept input from user input module 116 and database 120, while implementing algorithms for pathogen identification 122 and encryption 124. Processor 114 may also output data to a user output module 118 and/or data storage 126. Processor 114 may also output data to communication component 130, which in turn may pipe data to relevant entities 134 via communication network 132. The system may be powered by power supply 128. This approach is described in more detail below. All sequence data including but not limited to patient and microbial data may be encrypted to ensure patient privacy and may be encrypted so that it is secure. The system includes the ability to interact functionally with a remote data analysis center. This system may be capable of communicating via a network with relevant entities to drive cleaning intervention and provide information to determine medical intervention and treatment strategies.

Figure 2:
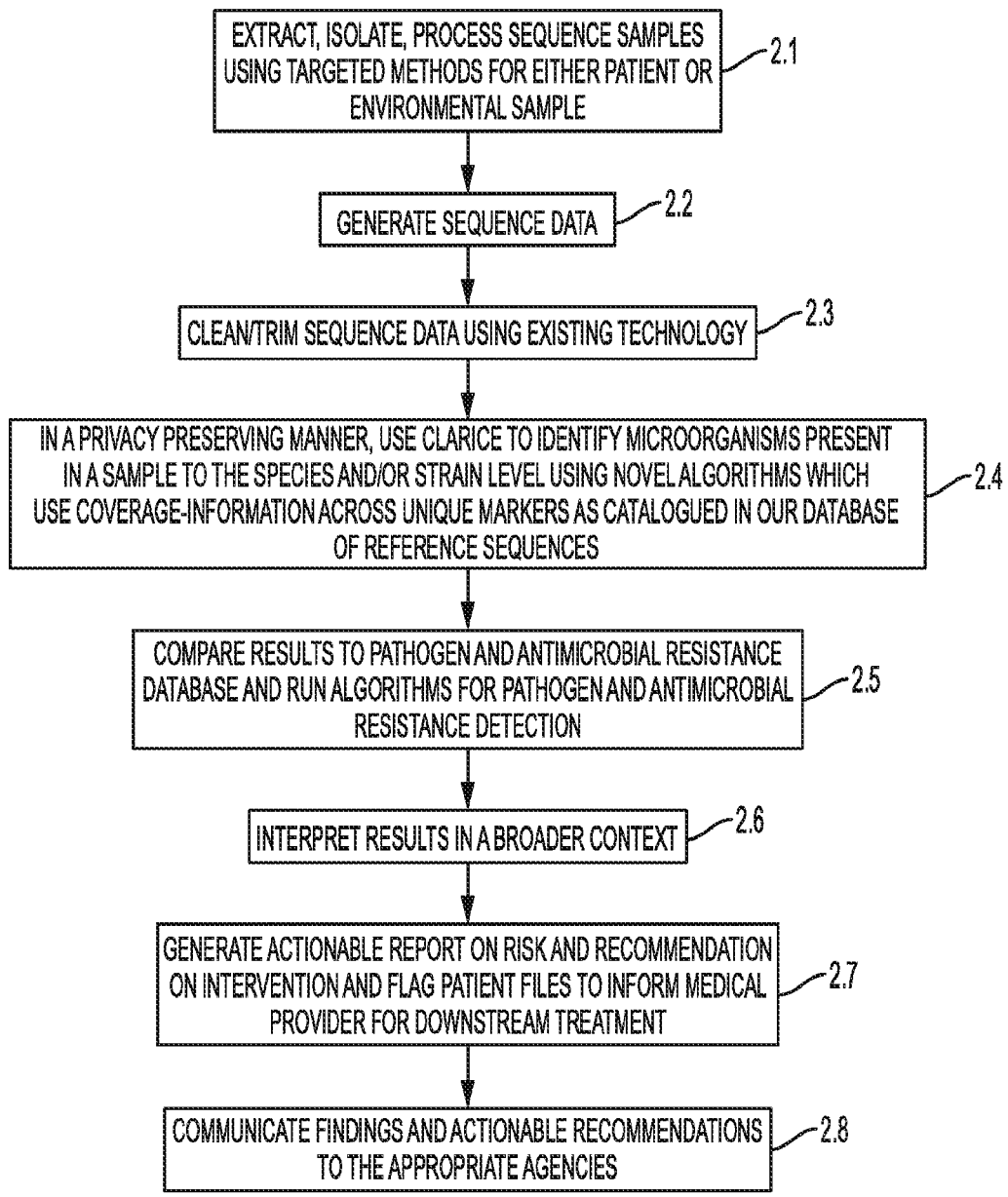
FIG. 2 is a flow chart illustrating the process of operation of the system of FIG. 1.

FIG. 2 is a flow chart illustrating the process of operation of the system of FIG. 1 (1.1). This process involves receiving environmentally- or patient-collected samples, extracting isolating, and processing these samples (2.1), generating DNA or RNA sequences for these samples which is stored in data storage (2.2). These sequence data are then cleaned/trimmed and processed further using existing technology and/or custom scripts (2.3). Processed sequence data are then fed into CLARICE to identify taxa and these taxa are identified in a privacy preserving manner in the case that one or several servers from the cloud are used to host the database (2.4). CLARICE results are compared to a pathogen and antimicrobial resistance database and are further processed using algorithms for pathogen and antimicrobial resistance detection (2.5). And these results are interpreted in a broader public health context including in comparison to other geographic and temporal samples and in the context of potential outbreaks facilitating tracking of pathogens and antimicrobial resistance (2.6). This system also generates actionable reports (2.7) on risk and generates recommendations on intervention and may facilitate the flagging of patient files to inform medical providers for downstream treatment. This system may also transmit and communicate findings and actionable recommendations to alert relevant entities as needed including a First Responder, Center for Disease Control (CDC), physicians, public health personnel, law enforcement and others (2.8). All datasets spanning steps 2.2 to 2.7 may be stored as either.

FIG. 3 is a flowchart depicting how an exemplary embodiment of the database of taxa-species and taxa-unique k-mers is identified given a k-mer length and a list of reference sequences and stored/saved in a computer hard disk. The first steps deal with the definition of k-mer length (e.g., an integer in the range between 17 and 32, or for larger values, for example an integer in the range between 32 and 79) and the list of all reference sequences (preferably located in the user computer disk, otherwise they may be accessed from a public server of curated DNA/RNA sequences of reference such as NCBI/RefSeq) with their taxonomic information (e.g., organism name, organism identifier against all other organisms, taxa id etc.). The last steps produce a database containing taxa-specific and taxa-unique k-mers given the list of reference sequences provided that it is stored and saved in disk that can be later on accessed and loaded directly in memory. The identification of taxa-specific and taxa-unique k-mers is defined as described next.

First, the program checks whether the database exists for the provided parameters (k-mer length and list of reference sequences). If the database already exists then the program can terminate. Otherwise, the program will create it and in order to do so, it starts by creating an empty database index (referred as "H" in the figure), which can typically be an hash-table or any other key-value storage. In the context of a key-value storage, the key is the k-mer (represented by its string value or its binary/numerical value) and the storage value may be a taxa identifier along with a "multiplicity count" (indicating how many taxa the k-mer in the key has been found). Then, the program reads all reference sequences and populates the database with k-mers as they are found in the sequences: For each reference sequence referred as "R", and for each k-mer referred as "w" existing in the reference sequences, the program checks (Step 3.1 in the figure) if w is already in the database. If it is, then the program reads what the taxa identifier found for w and if this taxa identifier is different from the identification of R then the program increments the multiplicity of w by 1, if w is not the database index the program creates a new value storage using w as the key and sets the taxa identifier to the identifier value from R and sets the multiplicity count to 1. Once the program has processed all reference sequences, it reads all k-mers inserted (Step 3.2) and remove all k-mers from the database that do have multiplicity count equal to 1. Then, in the Step 3.3, for each reference sequence R, the program removes each k-mers from R that is present in database more than once. Finally, in step 3.4, the program saves and stores in disk the remaining k-mers in the database index for each taxa. When storing the database in disk, the program also includes relevant information to recognize this database when the user presents the same k-mer length and the same list of reference sequences, so the program does not recompute/repeat the same calculations.

Figure 4A:
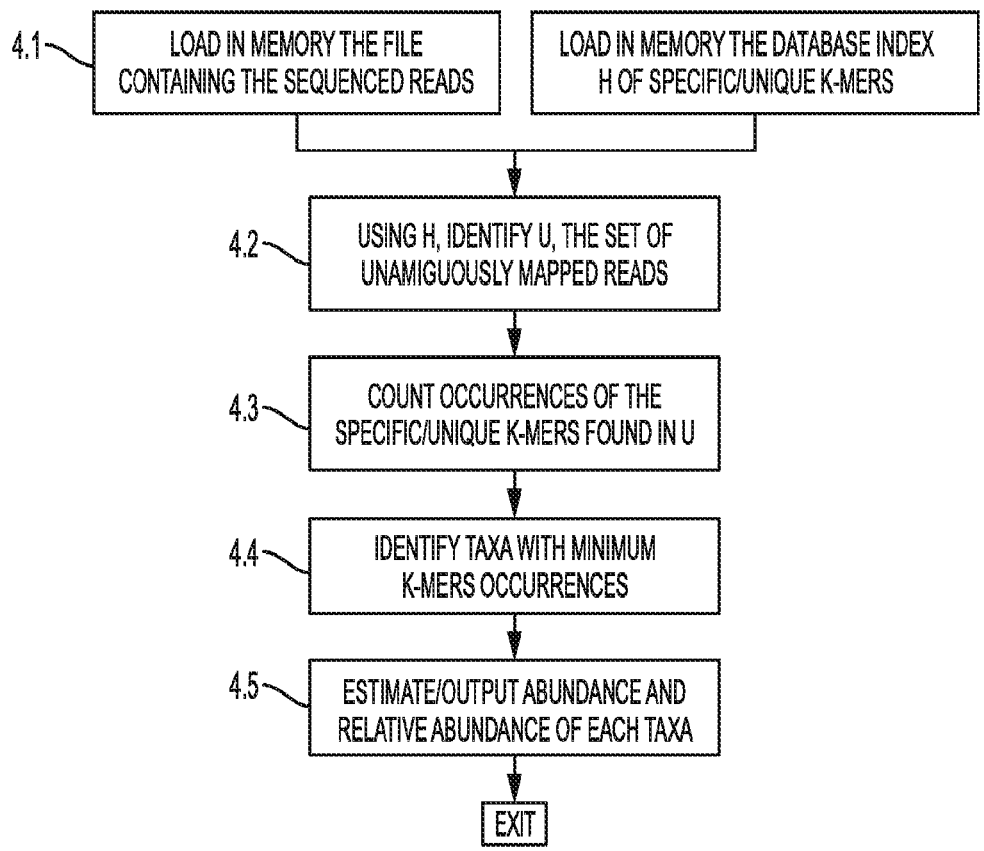
FIGS. 4A-4C depict schematics of the CLARICE algorithm.

FIG. 4A is a flowchart that describes an illustrative embodiment of the CLARICE algorithm with default settings. In step 4.0, the program loads in memory (or RAM) the database of taxa-specific and taxa-unique k-mers (with k defined by the user or by default, such as 19 or 21). This step is memory intensive and assumes that the user or operator analyzing the sample has access to a powerful server and that the program is run in it. In step 4.1, the user calls the algorithm with a sequenced sample from a targeted environment or patient that is loaded in memory to allow fast processing. In step 4.2, CLARICE attempts to identify all k-mers in each read thanks to the database of k-mers loaded in memory. Then, using the taxa-specific and unique k-mers, CLARICE identifies each read that is classified unambiguously using a generalized method from a recent work described in [Ounit and Lonardi, 2016]. This method is able, with extreme speed, to detect whether or not a read may be classified to the taxa S and to another taxa S' with an equally good mapping. In steps 4.3 to 4.5, CLARICE counts occurrences of the taxa-specific and taxa-unique k-mers found in the unambiguously mapped reads, and thus the abundance of each taxa T is estimated by a probabilistic model using the Poisson distribution or a mixture of probabilistic distribution from the counts of T-specific and T-unique k-mers.

Note that in this figure, the user does not provide any k-mer length value. It is because the optimal value for the k-mer length can be known in advance and thus set internally in the program. By default, k is 19 because the inventors' experiments and analysis shows that high performance in terms of speed, precision, sensitivity and memory usage occur for a value of k in the range (19-23). However, this algorithm may be extended/modified so the user can select a customized k-mer length between the 19 and 70, for example, k=23, k=25, k=27, k=29, k=31, k=33, k=35, k=37 or k=39.

In some embodiments, the program may select and process a fraction of the k-mers present in the sample or in the database in order to allow faster computations, to minimize communications with the server(s) and to enhance the privacy protection without loss of accuracy in the detection of microorganisms and their abundance estimations at the same time. The selection method of the k-mers may be based on clustering techniques of k-mers, estimation of information diversity in each k-mers or random sampling. This disclosure is based, at least in part, on the inventors' discovery that the identification and detection performance of the CLARICE algorithm remain stable and high even if a fraction of the k-mers present in the sample are used instead of all of them.

Figure 4B:
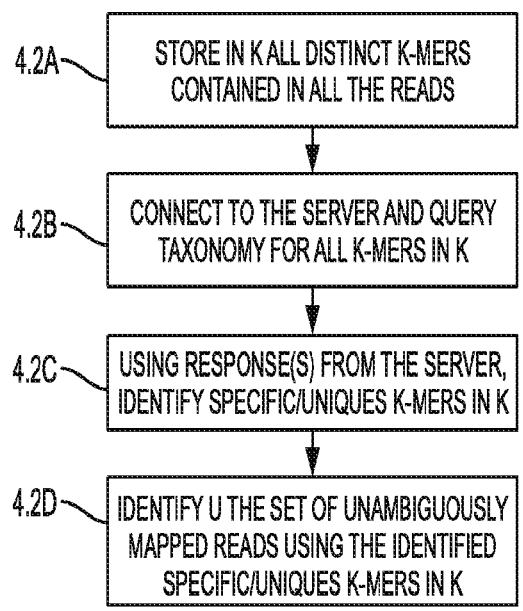

FIG. 4B is a flowchart that describes an exemplary variation of the schematic described in FIG. 4A. In this figure, it is assumed that the database of taxa-specific and taxa-unique k-mers is outsourced in a private/trusted server and CLARICE communicates with this server. While the core of the algorithm remains unchanged whether a powerful server is used, some variations exist and are detailed next. The step 4.0 described in the FIG. 4A is removed and not performed. In addition, the step 4.2 presented in FIG. 4A is the main step to be affected by this architecture with the server. Consequently, CLARICE collects all the k-mers in the sample and stores them in the container without repeat K. Then it queries the server for each of these k-mers in K in order to identify the taxa-specific and taxa-unique k-mers, and then proceeds to identify the reads that are unambiguously mapped (as described in the previous paragraph).

Figure 4C:
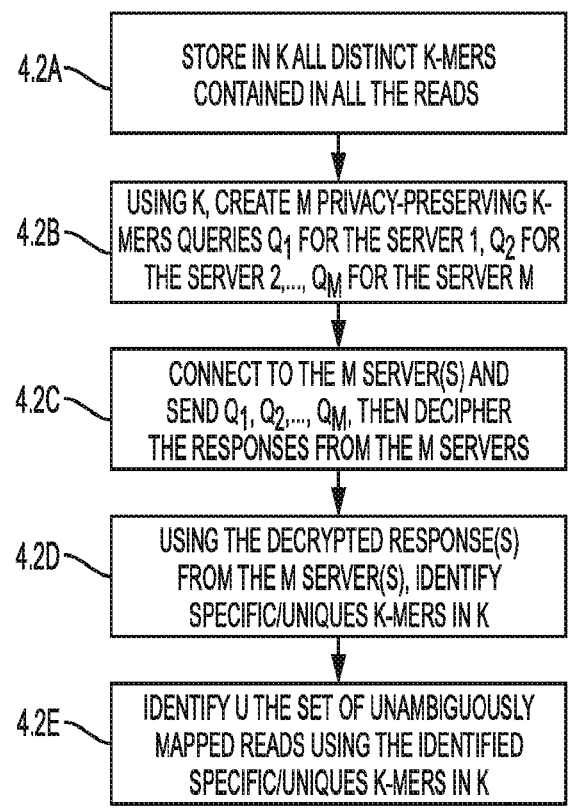

FIG. 4C is a flowchart that describes an illustrative variation of the schematic described in FIG. 4A. In this figure, it is assumed that the database of taxa-specific and taxa-unique k-mers is outsourced (fully or partially) in one or several (potentially untrusted) servers (say M servers, where M is higher than or equal to 1) and CLARICE communicates in a privacy-preserving manner with these servers. The step 4.0 described in the FIG. 4A is removed and not performed. The step 4.2 presented in FIG. 4A is the main step to be affected by this architecture with the M server(s). Consequently, CLARICE collects all the k-mers in the sample and store them without repeat in the container K. Then it creates privacy-preserving queries for each server so that the program can perform analysis of the k-mers in K without revealing the value or characteristics of these k-mers. These privacy preserving queries sent to each server may be different from one server to another, and/or may be created using encryption techniques, and/or obfuscations techniques, and/or may also be sets of range/index of the database index in the server(s) that the user may read and process locally. These queries are sent to the server(s) and each server processes these queries and returns responses that the user will post-process and/or decipher in order to identify organisms in which the queries k-mers were found. In order words, the program deciphers the responses from the servers to retrieve the taxa-specific and taxa-unique k-mers. Then, it proceeds to identify the reads that are unambiguously mapped (as described in the previous paragraph).

Figure 5:
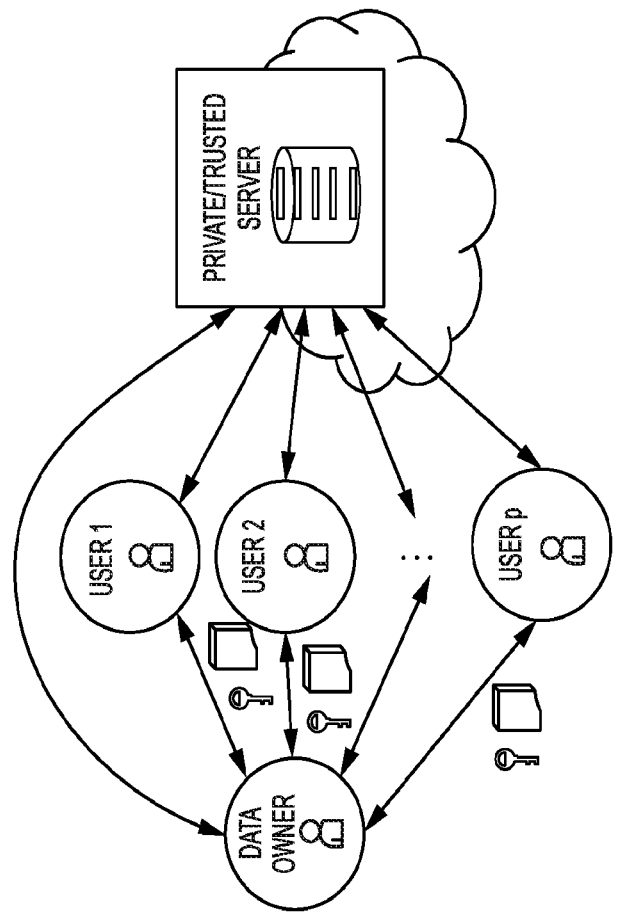
FIG. 5 presents a chart flow for the process of setting up the database in a private/trusted server by a data owner and the communication between one or several user(s) (each running CLARICE) and the server.
Figure 5:
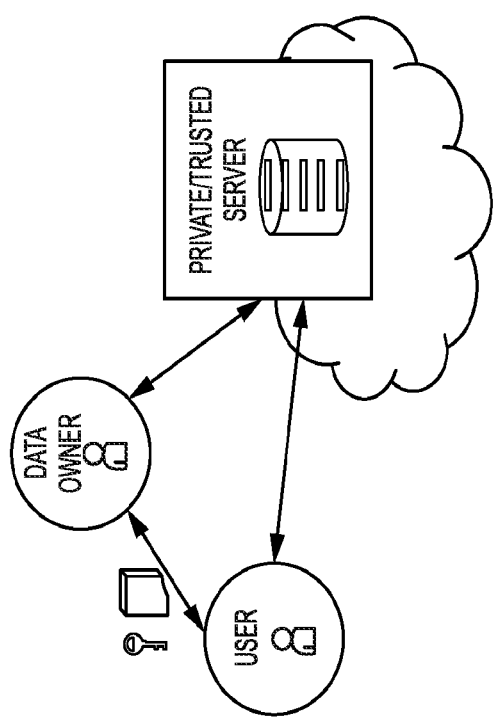

FIG. 5 presents a chart flow for the process of setting up the database in a private/trusted server by a data owner and the communication between one or several user(s) (each running CLARICE) and the server. The data owner sets up and stores in the server the database of taxa-specific and taxa-unique k-mers (that he/she has computed in a different and private server or the private/trusted server itself). The data owner also provides access parameters and security settings for the user(s) to connect to the private/trusted server. Using the settings and connections parameters provided by the data owner, the user(s) can communicate with the server and send queries. The data owner also provides access parameters and security settings for the user(s) so the CLARICE program running on the user side can connect to the private/trusted server. Using the settings and connection parameters provided by the data owner, the CLARICE program running on the user side communicates with the server and send can queries.

FIG. 6 describes a chart flow for the process of setting up the database by a data owner on one or several servers in the cloud that are potentially untrusted and the communication process between one user and the aforementioned server(s). The data owner sets up and stores on each server a database of encrypted taxa-specific and taxa-unique k-mers (that he/she has computed in a different and private server). The encrypted database stored in each of the M server(s) may not be identical to the one stored in another server. The data owner may even store only a limited portion of the encrypted database in one or several untrusted server(s). The data owner also provides access parameters and security settings for the user(s) to connect to the server(s). Using the settings and connection parameters provided by the data owner, the CLARICE program running on the user side can communicate with the server(s) and send privacy-preserving queries.

Figure 7:
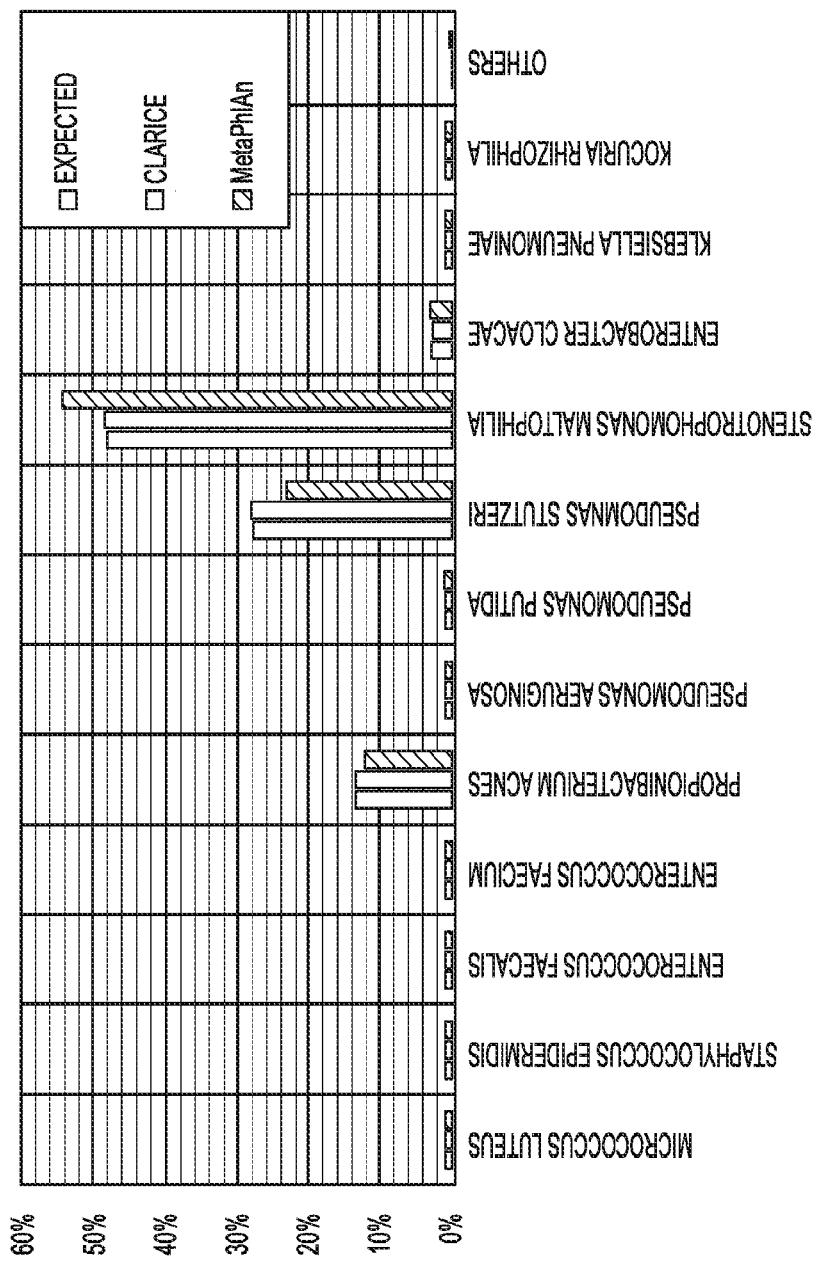
FIG. 7 presents the relative abundance of a synthetic dataset created to evaluate CLARICE, as well as the predictions from CLARICE and MetaPhlAn, a standard and popular metagenome analysis tool (so a strong competitor to CLARICE). This figure shows that CLARICE performs better than MetaPhlAn in accurately identifying species and their abundance in a synthetic dataset.

FIG. 7 shows the relative abundance estimations of the synthetic dataset (built with sequenced paired-end reads from twelve organisms, mostly pathogens, using a standard read generator) as well as the relative abundance estimations predicted by CLARICE and MetaPhlAn on the synthetic dataset. This figure shows CLARICE versus MetaPhlAn produced predictions and which fit best the real/expected estimations, indicating that CLARICE performs better than MetaPhlAn in accurately identifying species and their abundance in a synthetic dataset.

Figure 8:
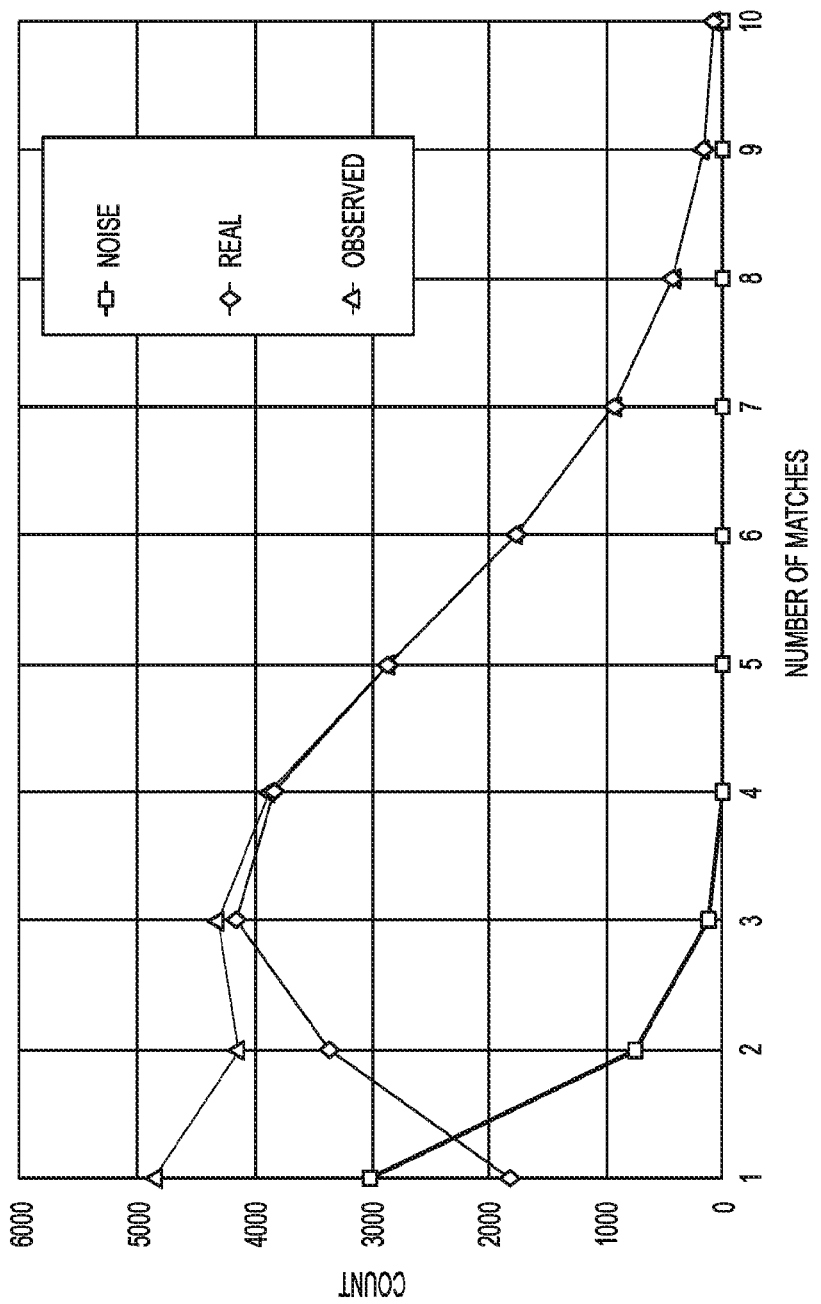
FIG. 8 presents an example of the observed distribution of the count of k-mers matches between the k-mers in a sequenced sample and the database of taxa-specific and taxa-unique. This figure considers the situation some k-mers matches occur due to sequencing errors and other noise.

FIG. 8 shows, for a given organism or taxon, an example of observed distribution of the count of k-mers matches between the k-mers in a sequenced sample and the database of taxa-specific and taxa-unique. This figure considers the situation some k-mers matches occur due to sequencing errors and other noise.

Table 1 shows the prediction of the relative abundance estimations by CLARICE and MetaPhlAn on a synthetic dataset. CLARICE predictions are the closest to the expected estimations. Indeed, the error-distance (using the L1 norm or "Manhattan" distance) of the predictions by CLARICE against the expected estimations is 0.8%, while the error-distance of the predictions by MetaPhlAn against the expected estimation is 13.2%, which is about 16 times higher than CLARICE's error. Table 1 shows that CLARICE performs better than MetaPhlAn in accurately identifying species and their abundance in the generated synthetic dataset (L1-distance from the expected abundance estimations is 13.2% for MetaPhlAn while it is only 0.82% for CLARICE).

TABLE 1

| Species name | Relative abundance estimations | | |
|---|---|---|---|
| | Expected | CLARICE | MetaPhlAn |
| Micrococcus luteus | 0.96% | 0.95% | 0.88% |
| Staphylococcus epidermidis | 0.96% | 0.96% | 0.98% |
| Enterococcus faecalis | 0.96% | 0.97% | 1.16% |
| Enterococcus faecium | 0.96% | 0.95% | 0.90% |
| Propionibacterium acnes | 13.46% | 13.44% | 12.09% |
| Pseudomonas aeruginosa | 0.96% | 0.93% | 0.84% |
| Pseudomonas putida | 0.96% | 0.94% | 1.00% |
| Pseudomonas stutzeri | 27.88% | 28.04% | 22.96% |
| Stenotrophomones maltophilia | 48.08% | 48.33% | 54.12% |
| Enterobacter cloacae | 2.88% | 2.68% | 2.90% |
| klebsiella pneumoniae | 0.96% | 0.91% | 0.90% |
| Kocuria rhizophila | 0.96% | 0.91% | 0.93% |
| Other species detected | 0.00% | 0.00% | 0.23% |
| Error against expected (L1-distance) | — | 0.82% | 13.2% |

Inferential statistical analyses of the genomic data may be combined with environmental and medical observations to further interpret results of this system and methods. This approach may be used to make recommendations to the appropriate entities to combat pathogens identified, such as recommendations on specific cleaning products to use, or the use of other preventative strategies and/or empiric antimicrobial therapy.

The processor (FIG. 1) may be an application-specific integrated circuit designed to achieve one or more specific functions or enable one or more specific devise or applications. The processor can receive DNA sequence data to be stored in a data store in memory. The data store can also include any suitable types or forms of memory for storing data in a form retrievable by the processor.

This system could also include a communication component to which the processor can send data retrieved from the data store. The communication component can include any suitable technology for communicating with the communication network, such as wired, wireless, satellite, etc. The system can communicate via a communication network (FIG. 1) with a variety of entities that may be relevant to notify in the event of a bioterrorist act or an epidemic outbreak. These entities can include a First Responder, Center for Disease Control (CDC), physicians, public health personnel, law enforcement and others.

Methods of Micro-Organismal Characterization

The methods and systems described in the current disclosure may use the shortest unique sequence information, which in a mixture of nucleic acids in an uncharacterized sample have the minimal unique length (n) with respect to the entire sequence information generated or collected. In addition to unique length sequences, non-unique may also be compared. The probability of identification of a genome increases with multiple matches. Some genomes will have longer minimal unique sequences than other genomes. The matching method of short length (n) sequences may continue in parallel with sequence information generation or collection. The comparisons occur as fast as (real-time) subsequent longer sequences are generated or collected. This results in considerable decision space reduction because the calculations are made early in terms of sequence information generation/collection. The probabilistic matching may include, but not limited to, perfect matching, subsequence uniqueness, pattern matching, multiple subsequence matching within n length, inexact matching, seed and extend, distance measurements and phylogenetic tree mapping. It may provide an automated pipeline to match the sequence information as fast as it is generated or in real-time. The sequencing instrument can continue to collect longer and more strings of sequence information in parallel with the comparison. Subsequent sequence information can also be compared and may increase the confidence of a genome or species identification in the sample. The method does not need to wait for sequence information assembly of the short reads into larger contigs.

In some embodiments, the system and methods may provide nucleic acid intake, isolation and separation, DNA sequencing, database networking, information processing, data storage, data display, and electronic communication to speed the delivery of relevant data to enable diagnosis or identification of organisms with applications for pathogenic outbreak and appropriate responses. In these embodiments, the system may include a portable sequencing device that electronically transmits data to a database for identification of organisms related to the determination of the sequence of nucleic acids and other polymeric or chain type molecules and probabilistic data matching. Embodiments include methods based on, but not limited to, Sequencing-by-synthesis, Sequencing-by-ligation, Single-molecule-sequencing and Pyrosequencing.

Probabilistic Methods and Techniques

In some embodiments, the present disclosure provides for systems and methods which employ a variety of probability-based techniques, models, and algorithms for determining the viability and risk of infection posed by any microorganism present in a sample.

Probabilistic Classification: The present disclosure may provide database engines, database design, filtering techniques and the use of probability theory as Extended Logic. The instant methods and system may utilize the probability theory principles to make plausible reasoning (decisions) on data produced by nucleic acid sequencing. Using the probability theory approach, the system described herein may analyze data as soon as it reaches a minimal number of nucleotides in length (k), and calculating the probability of the k-mer, further each subsequent increase in length (k+base pair(s)) is used to calculate the probability of a sequence match. The calculation of each k-mer and subsequent longer k-mers may be further processed to recalculate the probabilities of all increasing lengths to identify the presence of genome(s). As the unit length increases, multiple sub-units, within the k-mer are compared for pattern recognition, which further increases the probability of a match. Such method, including other Bayesian methods, provides for eliminating matches and identifying a significant number of biological samples comprising with a very short nucleotide fragment or read without having to complete full genome sequencing or assembling the genome. As such, assigning the likelihood of the match to existing organisms and move on to the next nucleic acid sequence read to further improve the likelihood of the match.

Probabilistic methods may also be used to build and query databases of genetic markers, including databases of the most unique regions of species genomes, antimicrobial resistance genes, virulence genes and phylogenetic markers. A probabilistic based statistical scoring approach may be used to assess matches between sample sequence and database, using a statistical score which represents the probability that a sequence match is a random occurrence based on the number of the total abundance of matches in the experimental spectrum.

Probability-based techniques underlie many of the population genetics models which will be utilized in this disclosure. For example, if $M_A$ ($M_a$) denotes the number of times allele A ($_a$) is sequenced, given that $L_A=1$ of k individuals in the sample have an allele of type A, the probability of detecting polymorphism is equal to the probability of reading at least one of the A and one of the remaining a alleles in the sample. Assuming that for each individual the number of reads at a particular locus is Poisson distributed with parameter $\lambda$, the probability of not covering the SNP locus for an individual is exp ($-\lambda$). This leads to the following probability for getting at least one A and one a read.

$$q_c(l,k,\lambda) := (1-[\exp(-\lambda)]^l)(1-[\exp(-\lambda)]^{k-1})$$

In order to build probabilistic classifiers to make a decision on short nucleic acid sequences, a variety of approaches to first filter and later classify the incoming sequencing data can be utilized. In the instant case, the formalism of Bayesian networks is utilized. A Bayesian network is a directed, acyclic graph that compactly represents a probability distribution. In such a graph, each random variable is denoted by a node (for example, in a phylogenetic tree of an organism). A directed edge between two nodes indicates a probabilistic dependency from the variable denoted by the parent node to that of the child. Consequently, the structure of the network denotes the assumption that each node in the network is conditionally independent of its non-descendants given its parents. To describe a probability distribution satisfying these assumptions, each node in the network is associated with a conditional probability table, which specifies the distribution over any given possible assignment of values to its parents. In this case a Bayesian classifier is a Bayesian network applied to a classification task of calculating the probability of each nucleotide provided by any sequencing system. At each decision point the Bayesian classifier can be combined with a version of shortest path graph algorithm such as Dijkstra's or Floyd's.

The current system may implement a system of Bayesian classifiers (for example, Naïve Bayesian classifier, Bayesian classifier and Recursive Bayesian estimation classifier) and fuse the resulting data in the decisions database. After the data is fused, each classifier may be fed a new set of results with updated probabilities.

The current system may implement a Bloom filter [Bloom et al, 1970]. A Bloom filter is a compact and probabilistic data structure used to indicate whether or not an element of interest is present in a set of elements. While this data-structure can return false positive, it does not return any false negatives. This data structure exploits hash functions, and the supported operations for example the insertion or removal of elements can be quickly performed. The current system may use and implement a Bloom filter for several specific operations. For example, a Bloom filter may be used to test whether or not an k-mer is present in the set of k-mers of a given taxa, or even to test whether this k-mers is present in the set of taxa-specific and taxa-unique k-mers of a given taxa. The program may also define and use variant Bloom filters, i.e., a data-structure that supports the same operations that the Bloom filter and that has the property of no false negative but that performs additional functions in order to achieve faster processing and/or less memory usage.

The system may use hash functions in several contexts and for several purposes, including the definitions of its internal data-structures (such as the Bloom filter). The system may use cryptographic hash functions, such as one or several in the set of functions in SHA-2 or "Secure Hash Algorithm 2" designed by the National Security Agency. A cryptographic hash function is a function that takes one input value and returns one output value, and that has the following properties: i) fast "digestion" of any input value, in order words, the function runs quickly for any element; ii) it is "collision-free", in order words, it is unlikely or extremely rare that the function returns the same output value for two different input values and iii) for any input value x, if y is the output value by the cryptographic hash function, then it is computationally difficult to retrieve x given y. The system may use one or several functions in the set of functions in SHA-2 (e.g., SHA-256) because these functions are considered secure and allows to process large input and output values.

The system may use fast similarity-estimation techniques such as MinHash [Broder, 1997] or min-wise independent permutations locality sensitive hashing scheme. A technique like MinHash may be used to determine with high speed, for example, how similar two sets of k-mers are to each other.

The system may use one or several techniques of data compression using exact of probabilistic models. These techniques of data compression may be used to allow fast and efficient communication between the server(s) and the user(s). The system may use the Burrows-Wheeler transform or "BWT" [Burrows and Wheeler, 1994] in order to achieve high compression on genomic data. The Burrows-Wheeler transform is an algorithm used in data compression techniques, and is widely used in several efficient sequence analysis programs. It rearranges a character string into runs of similar characters. It is useful for compression, since it tends to be easy to compress, and reversible without the need to store any additional data.

The system may use one or several suffix array(s) [Manber and Myers, 1990]. A suffix array is a space efficient data-structure based on a sorted array of all suffixes of a string. It is a data structure used for data compression and used in several bioinformatics applications.

Algorithms and Filters

Taxonomy Filter: Taxonomy filter has two main tasks: (i) Filter out as many organisms as possible to limit the classifier module to a smaller decision space, and (ii) Help determine the structure of the Bayesian network, which involves the use of machine learning techniques.

Phylogenetic tree filter: This sub-module of taxonomy filter interfaces with "Decisions Database" to learn the results of the previous round of analysis. If no results are found the module passes the new data to classification module. If the results are found the taxonomy filter adjusts classifier data to limit the possible decision space. For example if the prior data indicates that this is a virus DNA sequence that is being looked at, the decision space for the classifier will be shrunk to viral data only. This can be done by modifying the data Bayesian classifiers collected while operating.

Machine Learning: Machine learning algorithms are organized into a taxonomy, based on the desired outcome of the algorithm. (i) Supervised learning in which the algorithm generates a function that maps inputs to desired outputs. One standard formulation of the supervised learning task is the classification problem: the learner is required to learn (to approximate) the behavior of a function which maps a vector [X1, X2, ... XN] into one of several classes by looking at several input-output examples of the function. (ii) Semi-supervised learning which combines both labeled and unlabeled examples to generate an appropriate function or classifier. (iii) Reinforcement learning in which the algorithm learns a policy of how to act given an observation of the world. Every action has some impact in the environment, and the environment provides feedback that guides the learning algorithm. (iv) Transduction predicts new outputs based on training inputs, training outputs, and test inputs which are available while training. (v) Learning to learn in which the algorithm learns its own inductive bias based on previous experience.

Taxonomy Cache Module: The module caches taxonomy information produced by taxonomy filter. It can act as an interface between taxonomy filter and taxonomy database which holds all of the information in SQL database. Taxonomy cache is implemented as in-memory database with micro-second response timing. Queries to the SQL database are handled in a separate thread from the rest of the sub-module. Cache information includes the network graph created by the taxonomy filter module. The graph contains the whole taxonomy as the system starts analysis. DNA sequence analysis reduces the taxonomy graph with taxonomy cache implementing the reductions in data size and the removal of the appropriate data sets.

Classifier Selector: The instant system can utilize multiple classification techniques executing in parallel. Classifier selector can act as data arbiter between different classification algorithms. Classifier selector reads information from the Decisions Database and push such information to the classification modules with every DNA sequencing unit received for analysis from DNA Sequencing Module. Taxonomy filter acts as data pass through for the DNA sequencing data.

Recursive Bayesian Classifier: Recursive Bayesian classifier is a probabilistic approach for estimating an unknown probability density function recursively over time using incoming measurements and a mathematical process model. The module receives data from classifier selector and from the Decisions Database where prior decisions are stored. The data set is retrieved from the databases and prior decision identification placed in local memory of the module where the filtering occurs. The classifier takes DNA sequence and tries to match it with or without existing signatures, barcodes, etc., from the taxonomy database by quickly filtering out families of organisms that do not match. The algorithm works by calculating the probabilities of multiple beliefs and adjusting beliefs based on the incoming data. Algorithms used in this module may include Sequential Monte Carlo methods and sampling importance resampling. Hidden Markov Model, Ensemble Kalman filter and other particle filters may also be used together with Bayesian update technique.

Naïve Bayesian Classifier: Simple probabilistic classifier based on the application of the Bayes' theorem. The classifier makes all decisions based on the pre-determined rule-set which is provided as user input at start-up. The module can be re-initialized with a new rule set while it is executing analysis. New rules set can come from the user or it can be a product of the rules fusion of The Results Fusions module.

Bayesian Network Classifier: Bayesian Network Classifier implements a Bayesian network (or a belief network) as a probabilistic graphical model that represents a set of variables and their probabilistic independencies.

Decisions Database: Decisions Database is a working cache for most modules in the system. Most modules have direct access to this resource and can modify their individual regions. However only Results Fusion module can access all data and modify the Bayesian rule sets accordingly.

Bayesian Rules Data: The module collects all Bayesian rules in binary, pre-compiled form. The rules are read-write to all Bayesian classifiers as well as Taxonomy Filter and Results Fusions modules. The rules are dynamically recompiled as changes are made.

Results Fusion: The module fuses the date from multiple Bayesian classifiers as well as other statistical classifiers that are used. Results Fusion module looks at the mean variance between generated answers for each classifier and fuses the data if needed.

Database Interface: Interface to the SQL database. The interface is implemented programmatically with read and write functions separated in different threads. MySQL is the database of choice however sqLite may be used for faster database speed.

Taxonomy Database: The database will hold multiple internal databases: taxonomy tree, indexed pre-processed tree, user input and rules.

Cached Rules In-Memory cache of post-processed rules provided by the user.

Rules Management: Graphical Management Interface to the Module

User Input: User created inference rules. The rules are used by Bayesian classifiers to make decisions.

Security Protocols and Privacy-Preserving Techniques

The present disclosure may be based, at least in part, on the ability to protect without failure and with high efficiency the genomic content of the environmental/clinical sample(s) from any unwanted or unexpected data leak, data theft or data loss in the server(s) located in the cloud or during any communication between the user and users located in the cloud. Privacy protection is needed when using unknown or untrusted server(s) for outsourcing computations (see FIG. 6 and its description). To guarantee privacy, even when a server(s) is (are) untrusted or compromised, the present disclosure may rely on one or several secure protocols and/or encryption techniques, e.g., the private information retrieval protocol, the obfuscation protocol, the private set intersection protocol, homomorphic encryptions schemes (e.g., ElGamal encryption, RSA encryption) and Shamir secret sharing.

Private Information Retrieval protocol: a private information retrieval protocol Khor et al, 1995[1] is protocol that allows a user to secretly retrieve/read an item stored in a database. In order words, this protocol allows the users to retrieve an item without revealing to any database operator the desired item. One trivial, inefficient but perfectly secure approach is to send the user a copy of the entire database and let the user access it locally away from all database operators of the desired item. This protocol is inefficient because it requires obtaining all items of the database while only one item is desired. However, this protocol is perfectly secure because from the database perspective or from any database operator's point-of-view, all items of the database are equally the possible item of interest of the user, and thus no preference among the items is leaked to the database operator(s).

Obfuscation protocol: In the context of retrieving an item in a database, obfuscation protocols are an efficient and fast alternative to Private Information Retrieval protocols but they do provide a weaker guarantee of privacy. They merely try to obscure the identity of the item of interest by surrounding it with queries for other items (or "dummy items").

Private Set Intersection protocol: A private set intersection protocol is a protocol that allows one to determine the intersection of two sets or two databases, each owned by two different entities, operators or servers, A and B, without revealing elements that are not in the intersection. In order words, this protocol reveals only what A and B have in common.

Homomorphic encryption: this is an encryption protocol that allows computations to be carried out on ciphertext producing the encrypted result that, when decrypted, matches the result of operations performed on the plaintext. Encryption schemes that support this property are powerful because they allow an entity, potentially untrusted or malicious, to manipulate and perform, potentially memory-intensive, operations on encrypted data, without learning anything. This allows the possibility of outsourcing intensive computations of sensitive data by encrypting these data, sending the encrypted data to a potentially untrusted server in the cloud that can perform the intensive computations, and sending back the results, and finally deciphering the result. Examples of Homomorphic encryption systems are the RSA encryption or the ElGamal encryption described next.

ElGamal encryption: The ElGamal encryption system [ElGamal, 1985] is an asymmetric key encryption algorithm for public-key cryptography which is based on the Diffie-Hellman key exchange.

RSA encryption: is a standard cryptographic algorithm for exchanging messages in contemporary computer systems. Introduced in 1978, by Rivest, Shamir, and Adleman, it is an asymmetric encryption algorithm, exploiting the assumption that the factoring problem (i.e., decomposing an integer by its prime factor(s)) is computationally difficult.

Shamir secret sharing: this is an algorithm in cryptography able to shred a secret into a number of p distinct values and the secret can be recovered only if at least n (where n is lower or equal to p) of these values are known. Described in [Shamir, 1979], it is typically used for sharing a secret in several entities or parts (each participant has its own unique part) and some of the parts or all of them are needed in order to reconstruct the initial secret.

Advanced Encryption Standard: It is a standard in the encryption of electronic data by the US National Institute of Standards and Technology in 2001. Approved by the National Security Agency, it is a commonly and widely used encryption technique. It was initially invented by Rijmen and Daemen in 1998 and uses a cryptographic key of various sizes (i.e., 128, 192 and 256 bits).

The systems and methods of the disclosure are described herein as being embodied in computer programs having code to perform a variety of different functions. The code may be embodied on a non-transitory computer readable medium. Particular best-of-class technologies (present or emerging) can be licensed components. Existing methods for the extraction of DNA include the use of phenol/chloroform, salting out, the use of chaotropic salts and silica resins, the use of affinity resins, ion exchange chromatography and the use of magnetic beads. Methods are described in U.S. Pat. Nos. 5,057,426, 4,923,978, EP Patents 0512767 A1 and EP 0515484B and WO 95/13368, WO 97/10331 and WO 96/18731, the entire disclosures of which are hereby incorporated by reference. It should be understood, however, that the systems and methods are not limited to an electronic medium, and various functions can be alternatively practiced in a manual setting. The data associated with the process can be electronically transmitted via a network connection using the Internet. The systems and techniques described above can be useful in many other contexts, including those described below.

All viruses, bacteria and fungi contain DNA or RNA. The detection and sequencing of DNA or RNA from pathogens at the single molecule level could provide medically and environmentally useful information for the diagnosis, treatment and monitoring of infections and to predict potential drug resistance. Further opportunity will be in the arena of repeat-sequence applications where the methods are applied to the detection of subtle genetic variation.

Screening and Identification of Genome Sequences

The present disclosure is based, at least in part, on the ability to identify all, or nearly all, of the genomic sequences (including possible mutations and sequence variations) within a micro-organismal sample (e.g., mutations such as: translocations, inversions, large and small deletions and insertions, missense mutations, splice site mutations, etc.). In particular, these mutations or variations may be present in the genome of microorganisms of a sample, but not in normal colonies or the microorganisms. Such mutations are of particular interest if they lead to changes that result in a protein with an altered amino acid sequence that is unique to the microorganism's genome and subsequently affects viability and risk of infection. For example, useful mutations may include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence; and the like. Peptides with mutations or mutated polypeptides arising from, for example, splice-site, frameshift, read-through, or gene fusion mutations in tumor cells may be identified by sequencing DNA, RNA or protein in samples versus control or reference samples.

A number of initiatives are currently underway to obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Preferably, any suitable sequencing-by-synthesis platform can be used to identify mutations or genomic sequences. Four major sequencing-by-synthesis platforms are currently available: the Genome Sequencers from Roche/454 Life Sciences, the HiSeq Analyzer from Illumina/Solexa, the SOLiD system from Applied BioSystems, and the Heliscope system from Helicos Biosciences. Sequencing-by-synthesis platforms have also been described by Pacific Biosciences and VisiGen Biotechnologies. Each of these platforms can be used in the methods of the disclosure. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair. Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or in a step-and-repeat mode. For real-time analysis, different optical labels to each nucleotide may be incorporated and multiple lasers may be utilized for stimulation of incorporated nucleotides.

Any micro-organismal cell may be utilized to obtain nucleic acid samples for use in the sequencing methods described herein. In a preferred embodiment, the DNA or RNA sample is obtained after extracting samples from a public environment (e.g., hospital, mall, park, etc.). Alternatively, nucleic acid tests can be performed on dry samples (e.g. hair or skin).

A variety of methods are available for detecting the presence of a particular mutation or allele in micro-organismal DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present disclosure is understood to include all available methods.

Polymerase Chain Reaction (PCR) and other Amplification Techniques

PCR based detection may include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. In one embodiment, the single base polymorphism can be detected by using a specialized exonuclease-resistant nucleotide, as disclosed, e.g., U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the disclosure, a solution-based method is used for determining the identity of the nucleotide of a polymorphic site. Cohen et al. (French Patent No. 2,650,840; PCT Application No. WO1991/02087). As in the method of U.S. Pat. No. 4,656,127, a primer may be employed that is complementary to allelic sequences immediately 3' to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis or GBA® is described in PCT Application No. WO 1992/15712). GBA® uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO1991/02087) the GBA® method is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C, et al., Genomics 8:684-692 (1990); Kuppuswamy, M. N. et al., Proc. Natl. Acad. Sci.

(U.S.A.) 88: 1143-1147 (1991); Prezant, T. R. et al., Hum. Mutat. 1: 159-164 (1992); Ugozzoli, L. et al., GATA 9: 107-112 (1992); Nyren, P. et al., Anal. Biochem. 208: 171-175 (1993)). These methods differ from GBA® in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C, et al., Amer. J. Hum. Genet. 52:46-59 (1993)).

An alternative method for identifying changes in microbial viability and pathogenicity is direct protein sequencing. Protein sequencing of enzymatic digests using multidimensional MS techniques (MSn) including tandem mass spectrometry (MS/MS)) can also be used to identify microbial proteins of the disclosure. Such proteomic approaches permit rapid, highly automated analysis (see, e.g., K. Gevaert and J. Vandekerckhove, Electrophoresis 21: 1145-1154 (2000)). It is further contemplated within the scope of the disclosure that high-throughput methods for de novo sequencing of unknown proteins may be used to analyze the proteome of a micro-organismal sample to identify expressed proteins. For example, meta shotgun protein sequencing may be used to identify expressed proteins in a manner similarly applied to tumor antigens (see e.g., Guthals et al. (2012) Shotgun Protein Sequencing with Meta-contig Assembly, Molecular and Cellular Proteomics 11(10): 1084-96).

Peptide/Polypeptide Synthesis

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963).

A further aspect of the disclosure provides a nucleic acid (e.g., a polynucleotide) encoding a microorganismal peptide of the disclosure, which may be used to produce the peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. A still further aspect of the disclosure provides an expression vector capable of expressing a polypeptide according to the disclosure. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

The disclosure further embraces variants and equivalents which are substantially homologous to the identified microorganismal protein described herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

The disclosure also includes expression vectors comprising the isolated polynucleotides, as well as host cells containing the expression vectors. It is also contemplated within the scope of the disclosure that the microorganismal peptides may be provided in the form of RNA or cDNA molecules encoding the desired neo-antigenic peptides. The disclosure also provides that the one or more microorganismal peptides of the disclosure may be encoded by a single expression vector. The disclosure also provides that the one or more microorganismal peptides of the disclosure may be encoded and expressed in vivo using a viral based system (e.g., an adenovirus system).

The term "polynucleotide encoding a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the microorganismal peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide.

In embodiments, the polynucleotides can comprise the coding sequence for the microorganismal peptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the microorganismal peptides fused in the same reading frame to create a single concatamerized peptide construct capable of producing multiple peptides.

In embodiments, the present disclosure provides isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a microorganismal peptide of the present disclosure.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present disclosure, the parameters are set such that the percentage of identity is calculated over the full length of the reference nucleotide sequence and that gaps in homology of up to 5% of the total number of nucleotides in the reference sequence are allowed.

The isolated microorganismal peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the microorganismal peptides. Recombinant expression vectors are replicable DNA constructs which have synthetic or cDNA-derived DNA fragments encoding a microorganismal peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23: 175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a protein composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Modified products can be detected directly, or after a further reaction which creates products which are easily distinguishable. Means which detect altered size and/or charge can be used to detect modified products, including but not limited to electrophoresis, chromatography, and mass spectrometry. Other means which are reliant on specific sequences can be used, including but not limited to hybridization, amplification, sequencing, and ligase chain reaction. Combinations of such techniques can be uses as is desired. Examples of such chemical reagents for selective modification include hydrazine and bisulfite ions. Hydrazine-modified DNA can be treated with piperidine to cleave it. Bisulfite ion-treated DNA can be treated with alkali.

The ability to monitor the real-time progress of the PCR changes the way one approaches PCR-based quantification of DNA and RNA. Reactions are characterized by the point in time during cycling when amplification of a PCR product is first detected rather than the amount of PCR product accumulated after a fixed number of cycles. The higher the starting copy number of the nucleic acid target, the sooner a significant increase in fluorescence is observed. An amplification plot is the plot of fluorescence signal versus cycle number. In the initial cycles of PCR, there is little change in fluorescence signal. This defines the baseline for the amplification plot. An increase in fluorescence above the baseline indicates the detection of accumulated PCR product. A fixed fluorescence threshold can be set above the baseline. The parameter $C_T$ (threshold cycle) is defined as the fractional cycle number at which the fluorescence passes the fixed threshold. For example, the PCR cycle number at which fluorescence reaches a threshold value of 10 times the standard deviation of baseline emission may be used as $C_T$ and it is inversely proportional to the starting amount of target cDNA. A plot of the log of initial target copy number for a set of standards versus $C_T$ is a straight line. Quantification of the amount of target in unknown samples is accomplished by measuring $C_T$ and using the standard curve to determine starting copy number.

The entire process of calculating $C_{TS}$, preparing a standard curve, and determining starting copy number for unknowns can be performed by software, for example that of the 7700 system or 7900 system of Applied Biosystems. Real-time PCR requires an instrumentation platform that consists of a thermal cycler, computer, optics for fluorescence excitation and emission collection, and data acquisition and analysis software. These machines, available from several manufacturers, differ in sample capacity (some are 96-well standard format, others process fewer samples or require specialized glass capillary tubes), method of excitation (some use lasers, others broad spectrum light sources with tunable filters), and overall sensitivity. There are also platform-specific differences in how the software processes data. Real-time PCR machines are available at core facilities or labs that have the need for high throughput quantitative analysis.

Briefly, in the Q-PCR method the number of target gene copies can be extrapolated from a standard curve equation using the absolute quantitation method. For each gene, cDNA from a positive control is first generated from RNA by the reverse transcription reaction. Using about 1 μl of this cDNA, the gene under investigation is amplified using the primers by means of a standard PCR reaction. The amount of amplicon obtained is then quantified by spectrophotometry and the number of copies calculated on the basis of the molecular weight of each individual gene amplicon. Serial dilutions of this amplicon are tested with the Q-PCR assay to generate the gene specific standard curve. Optimal standard curves are based on PCR amplification efficiency from 90 to 100% (100% meaning that the amount of template is doubled after each cycle), as demonstrated by the slope of the standard curve equation. Linear regression analysis of all standard curves should show a high correlation ($R^2$ coefficient .gtoreq.0.98). Genomic DNA can be similarly quantified.

When measuring transcripts of a target gene, the starting material, transcripts of a housekeeping gene are quantified as an endogenous control. Beta-actin is one of the most used nonspecific housekeeping genes. For each experimental sample, the value of both the target and the housekeeping gene are extrapolated from the respective standard curve. The target value is then divided by the endogenous reference value to obtain a normalized target value independent of the amount of starting material.

The term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the disclosure are designed to be "substantially" complementary to each strand of the oligonucleotide to be amplified and include the appropriate nucleotides as discussed above. This means that the primers must be sufficiently complementary to hybridize with their respective strands under conditions that allow the agent for polymerization to perform. In other words, the primers should have sufficient complementarity with a 5' and 3' oligonucleotide to hybridize therewith and permit amplification of a nucleic acid sequence.

Primers of the disclosure are employed in the amplification process, which is an enzymatic chain reaction that produces exponentially increasing quantities of target locus relative to the number of reaction steps involved (e.g., polymerase chain reaction or PCR). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers used in disclosure methods may be prepared using any suitable method, such as conventional phosphotriester and phosphodiester methods or automated embodiments thereof. In one such automated embodiment, diethylphos-phoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

The primers of the disclosure embrace oligonucleotides of sufficient length and appropriate sequence so as to provide specific initiation of polymerization on a significant number of nucleic acids in the polymorphic locus. Where the nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

As described herein, any nucleic acid specimen, in purified or nonpurified form, can be utilized as the starting nucleic acid or acids, provided it contains, or is suspected of containing, the specific nucleic acid sequence containing the target locus.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the disclosure is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90 C-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

In certain preferred embodiments, the agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2× SSC/0.1% SDS at about room temperature (low stringency conditions); 0.2× SSC/0.1% SDS at about 42° C. (moderate stringency conditions); and 0.1× SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Preferably, the method of amplifying is by PCR, as described herein and as is commonly used by those of ordinary skill in the art. Alternative methods of amplification have been described and can also be employed as long as the methylated and non-methylated loci amplified by PCR using the primers of the disclosure are similarly amplified by the alternative means.

The amplified products are preferably identified by sequencing. Sequences amplified by the methods of the disclosure can be further evaluated, detected, cloned, sequenced, and the like, either in solution or after binding to a solid support, by any method usually applied to the detection of a specific DNA sequence such as PCR, oligomer restriction, allele-specific oligonucleotide (ASO) probe analysis, oligonucleotide ligation assays (OLAs), and the like.

One may use MALDI mass spectrometry in combination with a detection assay to observe the size of a nucleic acid product. The principle behind mass spectrometry is the ionizing of nucleic acids and separating them according to their mass to charge ratio. Similar to electrophoresis, one can use mass spectrometry to detect a specific nucleic acid that was created in an experiment.

One form of chromatography, high performance liquid chromatography, is used to separate components of a mixture based on a variety of chemical interactions between a substance being analyzed and a chromatography column. DNA is first treated with sodium bisulfite, which converts an unmethylated cytosine to uracil, while methylated cytosine residues remain unaffected. One may amplify the region containing potential methylation sites via PCR and separate the products via denaturing high performance liquid chromatography (DHPLC). DHPLC has the resolution capabilities to distinguish between methylated (containing cytosine) and unmethylated (containing uracil) DNA sequences. (See Deng, D. et al. Simultaneous detection of CpG methylation and single nucleotide polymorphism by denaturing high performance liquid chromatography. 2002 Nuc Acid Res, 30, 3.)

Hybridization is a technique for detecting specific nucleic acid sequences that is based on the annealing of two complementary nucleic acid strands to form a double-stranded molecule. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An additional method of sequencing would be to sequence the DNA to directly observe any modifications. Pyrosequencing technology is a method of sequencing-by-synthesis in real time. It is based on an indirect bioluminometric assay of the pyrophosphate (PPi) that is released from each deoxynucleotide (dNTP) upon DNA-chain elongation. This method presents a DNA template-primer complex with a dNTP in the presence of an exonuclease-deficient Klenow DNA polymerase. The four nucleotides are sequentially added to the reaction mix in a predetermined order. If the nucleotide is complementary to the template base and thus incorporated, PPi is released. The PPi and other reagents are used as a substrate in a luciferase reaction producing visible light that is detected by either a luminometer or a charge-coupled device. The light produced is proportional to the number of nucleotides added to the DNA primer and results in a peak indicating the number and type of nucleotide present in the form of a pyrogram. Pyrosequencing can exploit the sequence differences that arise.

A variety of amplification techniques may be used in a reaction for creating distinguishable products. Some of these techniques employ PCR. Other suitable amplification methods include the ligase chain reaction (LCR) (Barringer et al, 1990), transcription amplification (Kwoh et al. 1989; WO88/10315), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO90/06995), nucleic acid based sequence amplification (NASBA) (U.S. Pat. Nos. 5,409,818; 5,554,517; 6,063,603), nick displacement amplification (WO2004/067726).

One way to distinguish between modified and unmodified DNA is to hybridize oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not. The amplification products can be optionally hybridized to specific oligonucleotide probes which may also be specific for certain products. Alternatively, oligonucleotide probes can be used which will hybridize to amplification products from both modified and non-modified DNA.

Another way to distinguish between modified and non-modified DNA is to use oligonucleotide probes which may also be specific for certain products. Such probes can be hybridized directly to modified DNA or to amplification products of modified DNA. Oligonucleotide probes can be labeled using any detection system known in the art. These include but are not limited to fluorescent moieties, radio-isotope labeled moieties, bioluminescent moieties, luminescent moieties, chemiluminescent moieties, enzymes, substrates, receptors, or ligands.

Real time chemistry allows for the detection of PCR amplification during the early phases of the reactions, and makes quantitation of DNA and RNA easier and more precise. A few variations of the real-time PCR are known. They include the TAQMAN system and MOLECULAR BEACON system which have separate probes labeled with a fluorophore and a fluorescence quencher. In the SCORPION system the labeled probe in the form of a hairpin structure is linked to the primer.

Any specimen containing a detectable amount of polynucleotide or antigen can be used. Preferably the subject is human.

Samples

Samples for use in the methods of the disclosure include cells or tissues obtained from water, surfaces (i.e., walls, tables, beds, chairs, armrests, stools, counter-tops, instruments, screens, monitors, computers, floors, door handles, doors, windows, screens, pillows, cabinets, cabinet doors, sinks, faucets, etc.), blood, blood plasma, serum, cells, a cellular extract, a cellular aspirate, lung lavage, expectorant, sputum, saliva, mucous, urine, sweat, tears, and/or any bodily fluid.

Any nucleic acid specimen, in purified or nonpurified form, can be utilized as the starting nucleic acid or acids, provided it contains, or is suspected of containing, the specific nucleic acid sequence containing the target locus (e.g., genes or gene products related to determining viability and/or risk of causing infection). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing sample or specimen used for detection of certain gene characteristics may be extracted by a variety of techniques such as that described by Maniatis, et al. (Molecular Cloning: A Laboratory Manual, Cold Spring Harbor, N.Y., pp 280, 281, 1982).

If the extracted sample is impure (e.g., plasma, serum, stool, ejaculate, sputum, saliva, ductal cells, nipple aspiration fluid, ductal lavage fluid, cerebrospinal fluid or blood or a sample embedded in paraffin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (Saiki et al., (1988) Science 239:487-491) and by U.S. Pat. Nos. 4,683,195, 4,683,202 and 4,800,159, each of which is incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, *Thermus aquaticus* or *Thermococcus litoralis* DNA polymerases which eliminate the need to add enzyme after each denaturation cycle, are commercially available. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, *Escherichia coli* DNA polymerase I, Klenow fragment of *E. coli* polymerase I, T4 DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Q.beta. replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NITROPURE) or other membranes used in for detection of gene expression such as polyvinylchloride, diazotized paper and other commercially available membranes such as GENESCREEN, ZETAPROBE. (Biorad), and NYTRAN. Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2× SSC/0.1% SDS at about room temperature (low stringency conditions); 0.2× SSC/0.1% SDS at about 42° C. (moderate stringency conditions); and 0.1× SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

The following examples are offered by way of illustration, not by way of limitation. While specific examples have been provided, the above description is illustrative and not restrictive. Any one or more of the features of the previously described embodiments can be combined in any manner with one or more features of any other embodiments in the present disclosure. Furthermore, many variations of the disclosure will become apparent to those skilled in the art upon review of the specification. The scope of the disclosure should, therefore, be determined not with reference to the above description, but instead should be determined with reference to the appended claims along with their full scope of equivalents.

It should be appreciated that the disclosure should not be construed to be limited to the examples that are now described; rather, the disclosure should be construed to include any and all applications provided herein and all equivalent variations within the skill of the ordinary artisan.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

EXAMPLES

Example 1

Coverage Informed KMER Analysis to Classify and Contain Nosocomial Pathogens

Purpose: The use of a novel algorithm to rapidly identify taxa and estimate abundance with high confidence in mixed-microorganismal samples. For a single microorganismal (or a mix-microorganismal sample which has been processed to isolate a single species through culturing) sample, the whole genome is analyzed using complementary approaches. One approach includes calculating the sequence coverage over unique and specific kmers in the generated novel and comprehensive database. This approach is based on the understanding that if a species is present in a sample one can expect even coverage across that species' genome because sequencing should occur randomly across the genome. This approach improves one's ability to reliably classify species because it sidesteps many computational problems found in current bioinformatic tools and shifts the analysis from a "gene-centric" metagenomic approach to a "genome-centric" approach [Prosser 2015]. In this example, classification of important pathogens and characterization of abundance are then used to prevent the spread of infection in a healthcare environment.

Method: For this example, a synthetic dataset was generated which includes 17 species which fit two criteria 1) in the inventor's experimental work, these species have been found to be most abundant in healthcare environments on surfaces, and/or 2) they are top pathogens that cause patients to contract nosocomial infections from healthcare surfaces based on CDC reports. This approach, of generating a synthetic dataset informed by the inventors' experimental results, was designed to build synthetic datasets which are realistic and expected to be found in healthcare environments (e.g. do not contradict ecological community assembly rules with species which may realistically coexist in a healthcare setting in the relative abundances discovered). This approach presents a stronger example of the realistic application of this disclosure to be a useful way to classify and shape the response of healthcare workers to infectious disease. Specifically, to identify which species to focus on in this example, samples were collected from 398 ambulances across the United States, and similarly to the laboratory and computational protocols outlined in this disclosure (FIG. 1, FIG. 2), extracted and purified DNA, conducted library prep and sequenced on an Illumina HiSeq 2500. Low quality sequences were removed (<Q20) and adaptors trimmed. Data were then analyzed using available classification tools including MetaPhlAn [Segata et al, 2012] and CLARK

[Ounit 2015]. To increase confidence in classification the overlapping results between these two tools was used for further analysis. From this overlapping dataset samples were selected to be used to inform synthetic dataset creation, including samples with high levels of important nosocomial pathogens.

Including the species identified in the inventors' experimental work, synthetic paired-end sequence data was generated using a bioinformatics tool ART [Huang et al, 2012], a standard read generator, using default settings with a sequencing error rate consistent with an Illumina HiSeq 2500.

To compare both CLARICE's ability to classify these species and estimate abundance compared to the expected results as well as compared to a leading classification tool MetaPhlAn, this synthetic dataset was analyzed using CLARICE and MetaPhlAn using default setting for both tools.

FIG. 7 compares CLARICE results to MetaPhlAn results, including best fit predictions for real/expected estimations. This figure indicates that CLARICE performs better than MetaPhlAn in accurately identifying species and their abundance in a synthetic dataset.

These results would be presented to the appropriate organizations (e.g. this system may transmit and communicate findings and actionable recommendations to alert relevant entities as needed including a First Responder, Center for Disease Control (CDC), physicians, public health personnel, law enforcement and others). If these data were collected from a hospital environment as part of a hospital surveillance program an actionable report would be generated recommending recleaning of the area using a bleach-based disinfectant and the flagging of the patient file to inform health care providers of exposure of patients to the specific nosocomial pathogens listed.

Example 2

Evaluation of the Depth or Abundance of an Organism (or Taxon) Using a Probabilistic Model The abundance, depth or coverage of the taxon S present in a sequenced sample is estimated by analyzing the distribution of the count of matches between the k-mers present in the unambiguously mapped reads to S and the set of k-mers specific and unique to S from the database. Because only specific and unique k-mers to S are considered, this distribution is expected to be a Poisson distribution of parameter the abundance of S in the sample. However, some noisy matches or matches that occurred because of sequencing errors, genomic variations or sequencing noises can bias and interfere with the theoretical or "real" Poisson distribution. In such a situation (see FIG. 8), the observed or experimental Poisson distribution is the sum of two Poisson distributions: a first distribution modeling the noisy signal (modeled by a Poisson distribution of parameter u such that usually $u \leq 1$) and a second modeling the real signal (modeled by a Poisson distribution of parameter c, the abundance of S). These two signals can be easily detected and separated if c is significantly higher than 1 (e.g., 3 or more) by analyzing the derivatives of the curve to identify any peak or hump in the curve. In the case a peak or hump in the curve is found at a number of matches x, then the abundance c is estimated as $(C(x)*x/C(x-1)+C(x+1)*(x+1)/C(x)+C(x+2)*(x+2)/C(x+1))/3$, where $C(x)$ is the number of k-mers being matched exactly x times. If no peak or hump is found then the abundance is estimated as $C(2)*2/C(1)$.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

REFERENCES

Allen, H. K., Moe, L. A., Rodbumrer, J., Gaarder, A., and Handelsman, J. Functional metagenomics reveals diverse β-lactamases in a remote alaskan soil. The ISME journal, 3(2):243-251, 2009.

Bloom, B. H., Space/Time Trade-offs in Hash Coding with Allowable Errors, Communications of the ACM, 13 (7): 422-426, 1970.

Broder, A. Z., On the resemblance and containment of documents, Compression and Complexity of Sequences: Proceedings, Positano, Amalfitan Coast, Salerno, Italy, Jun. 11-13, 1997, IEEE, pp. 21-29, 1997.

Burrows, M., Wheeler, D. J., A block sorting lossless data compression algorithm, Technical Report 124, Digital Equipment Corporation, 1994.

Chor, B. Goldreich, O. Kushilevitz, E. and Sudan, M., Private information retrieval, Proceedings of the 36th Annual Symposium on Foundations of Computer Science, 1995.

ElGamal T., A Public-Key Cryptosystem and a Signature Scheme Based on Discrete Logarithms. IEEE Transactions on Information Theory. 31 (4): 469-472, 1985.

Erlich, Y. and Narayanan, A., Routes for breaching and protecting genetic privacy. *Nature Reviews Genetics,* 15(6). pp.409-421, 2014.

Franzosa, E. A., Huang, K, Meadow, Gevers, D., Lemon, K, Bohannan, B. J., Huttenhower, C., Identifying personal microbiomes using metagenomic codes. Proceedings of the National Academy of Sciences, 112(22): E2930-8, 2015.

Gymrek, M., McGuire, A. L., Golan, D., Halperin, E. and Erlich, Y., Identifying personal genomes by surname inference. *Science,* 339(6117), pp.321 -324, 2013.

Homer N, Szelinger S, Redman M, Duggan D, Tembe W, Muehling J, Pearson J V, Stephan D A, Nelson S F, Craig D W, Resolving individuals contributing trace amounts of DNA to highly complex mixtures using high-density SNP genotyping microarrays. PLoS Genet. 2008 Aug. 29; 4(8):e1000167.

Huang, W., Li, L., Myers, J. R., and Marth, G. T., Art: a next-generation sequencing read simulator. Bioinformatics, 28(4), 593-594, 2012

Jones, K. E., Patel, N. G., Levy, M. A., Storeygard, A., Balk, D., Gittleman, J. L., and Daszak, P. Global trends in emerging infectious diseases. Nature, 451(7181):990-993, 2008.

Manber, U., Myers, G., Suffix arrays: a new method for on-line string searches. First Annual ACM-SIAM Symposium on Discrete Algorithms. pp. 319-327, 1990.

Martinez, J. L. Antibiotics and antibiotic resistance genes in natural environments. Science, 321(5887): 365-367, 2008.

Martiny, A. C., Martiny, J. B., Weihe, C., Field, A., and Ellis, J. C. Functional metagenomics reveals previously unrecognized diversity of antibiotic resistance genes in gulls. Frontiers in microbiology, 2, 2011.

Ounit, R., Wanamaker, S., Close, T. J., and Lonardi, S. Clark: fast and accurate classification of metagenomic and genomic sequences using discriminative k-mers. BMC genomics, 16(1):1, 2015.

Ounit, R., and Lonardi, S. Higher classification sensitivity of short metagenomic reads with clark-s. Bioinformatics, btw542, 2016.

J. I. Prosser, Dispersing misconceptions and identifying opportunities for the use of 'omics' in soil microbial ecology. Nature Reviews Microbiology, 13(7): 439-46, 2015.

Rivest, R., Shamir, A., Adleman, L., A Method for Obtaining Digital Signatures and Public-Key Cryptosystems. Communications of the ACM 21 (2): 120-126, 1978

Segata, N., Waldron, L., Ballarini, A., Narasimhan, V., Jousson, O., and Huttenhower, C. Metagenomic microbial community profiling using unique clade-specific marker genes. Nature methods, 9(8), 811-814, 2012.

Shamir, A., How to share a secret, Communications of the ACM, 22 (11): 612-613. 1979.

Sobih, A., Tomescu, A. I., Makinen, V., MetaFlow: Metagenomic profiling based on whole-genome coverage analysis with min-cost flows. bioRxiv, 2016.

What is claimed is:

1. A method, comprising:
    i) a process of building a database by a data owner, comprising
        building a reference k-mer database of taxa specific markers and taxa unique markers; and
        setting up the reference k-mer database in at least one server wherein each server stores at least a portion of the database;
    ii) a process of searching the database by a user, comprising
        obtaining a sample including one or more microorganism populations;
        wherein the sample is obtained from a subject;
        generating, by a control unit including a memory and a processor, nucleic acid sequence data for the one or more microorganism populations;
        determining, by the control unit, a set of k-mers of one or more nucleic acid regions from the one or more microorganism populations;
        communicating to the at least one server and comparing, by the control unit, the set of k-mers to the reference k-mer database of taxa-specific markers and taxa unique markers, wherein the at least one server comprises a private or trusted server or a public server or cloud-based server, wherein, when the at least one sever comprises a public server or cloud-based server, the communicating step is under a privacy-preserving scheme;
        assigning each k-mer to a taxon only if it is impossible to assign the k-mer to another taxon with the same mapping quality or assignment quality;
        filtering, by the control unit, the nucleic acid sequence data that do not map unambiguously to one and only one organism to provide a set of taxa-specific and taxa-unique k-mers found in unambiguously mapped sequence reads, wherein the filtering does not cause loss of identification performance or accuracy;
        determining, by the control unit, depth of sequence coverage of taxa specific sequences to identify one or more taxa from the one or more microorganism populations;
        modeling, by the control unit, the frequency of k-mers in the sequenced sample that match the database using one or several probabilistic models per taxon; and
        modeling, by the control unit, the distribution of the frequency of the taxa-specific and taxa-unique k-mers found in unambiguously mapped sequence reads using one or more probabilistic models to estimate abundance of each identified one or more taxa, wherein the model utilizes a Poisson distribution or a mixture of probabilistic distribution from counts of occurrences of the taxa-specific and taxa-unique k-mers found in the unambiguously mapped reads to estimate the abundance of the one or more taxa; thereby identifying the one or more microorganism populations in the samples; and
    iii) administering to the subject a suitable treatment comprising an empiric antimicrobial therapy including one or more of antibiotics, antivirals, antifungals, antiprotozoals, and antihelminthics that appropriately eliminates the one or more microorganism populations identified in the sample.

2. The method of claim 1, wherein the probabilistic model increases confidence.

3. The method of claim 1, wherein the set of k-mers includes at least 10 individual k-mers.

4. The method of claim 1, wherein the set of k-mers includes at least 100 individual k-mers.

5. The method of claim 1, wherein a subset of the reference database is used that corresponds to the sample source, whether patient or environmentally collected, to increase confidence while maximizing analysis speed.

6. The method of claim 1, wherein the set of k-mers includes a plurality of k-mers each ranging from about 17 to about 63 nucleotides in length.

7. The method of claim 1, wherein the set of k-mers includes a plurality of k-mers each ranging from about 17 to about 31 nucleotides in length.

8. The method of claim 1, wherein the obtained sample comprises DNA or RNA.

9. The method of claim 1, wherein the nucleic acid sequence(s) from which the nucleic acid sequence data are obtained may be amplified prior to determining a k-mer set to use in analysis.

10. The method of claim 1, wherein the privacy-preserving scheme comprises at least one of a private information retrieval protocol, an obfuscation protocol, a private set intersection protocol, a homomorphic encryptions scheme, and Shamir secret sharing.

11. The method of claim 1, wherein the process in step ii) further comprises
    comparing the identified one or more taxa in the sample to taxa in other geographic and temporal samples and/or in the context of potential outbreaks of pathogens and antimicrobial resistance, thereby interpreting the identified one or more taxa in a broader public health context.

12. The method of claim 1, wherein the process in step ii) further comprises
    transmitting the identified one or more taxa in the sample and/or actionable recommendations to at least one relevant entity comprising a First Responder, physicians, public health personnel, and/or law enforcement.

13. The method of claim 1, wherein the one or more microorganism populations in the sample comprises one or more of *Clostridium difficile, Staphylococcus aureus* (including Methicillin resistant strains (MRSA)), *Klebsiella pneumoniae, Klebsiella oxytoca, Escherichia coli, Enterococcus* species (including *E. faecalis* and *E. faecium* and Vancomycin-resistant Enteroccus (VRE)), *Pseudomonas aeruginosa, Candida* species (including *C. albicans, C. parapsilosis*, and *C. glabrata*), *Streptococcus* species, Coagulase-negative *staphylococcus* species, *Enterobacter* species, *Acinetobacter baumannii, Proteus mirabilis, Stenotrophomonas maltophilia, Citrobacter species, Serratia species, Bacteroides species, Haemophilus* species, adenovirus, herpes simplex virus, parainfluenza virus and norovirus, *Peptostreptococcus* species, additional *Klebsiella* species, additional *Clostridium* species, *Prevotella* species, *Morganella morganii, Lactobacillus* species, Avian influenza virus, swine influenza virus, Zika virus, West Nile virus, Ebola virus, *plasmodium* species, yellow fever virus, Dengue virus, Lassa virus, Human immunodeficiency virus, *Vibrio cholerae*, Middle East respiratory syndrome coronavirus (MERS-COV), *Mycobacterium tuberculosis, Borrelia burgdorferi, Yersinia pestis*, or a virus causative of viral hepatitis.

14. A method, comprising:
   i) a process of building a database by a data owner, comprising
      building a reference k-mer database of taxa specific markers and taxa unique markers; and
      setting up the reference k-mer database in at least one server, wherein each server stores at least a portion of the database; and
   ii) a process of searching the database by a user, comprising
      obtaining a sample at a location including one or more microorganism populations at one or more time points
         wherein the sample is obtained from a subject, or the sample is an environmental sample;
      generating, by a control unit including a memory and a processor, nucleic acid sequence data for the one or more microorganism populations at each of the one or more time points;
      determining, by the control unit, a set of k-mers of one or more nucleic acid regions from the one or more microorganism populations;
      communicating to the at least one server and comparing, by the control unit, the set of k-mers to the reference k-mer database of taxa-specific markers and taxa unique markers, wherein the at least one server comprises a private or trusted server or a public server or cloud-based server, wherein, when the at least one server comprises a public server or cloud-based server, the communicating step is under a privacy-preserving scheme;
      assigning each k-mer to a taxon only if it is impossible to assign the k-mer to another taxon with the same mapping quality or assignment quality;
      filtering, by the control unit, the nucleic acid sequence data that do not map unambiguously to one and only one organism to provide a set of taxa-specific and taxa-unique k-mers found in unambiguously mapped sequence reads, wherein the filtering does not cause loss of identification performance or accuracy;
      determining, by the control unit, depth of sequence coverage of taxa specific sequences to identify one or more taxa from the one or more microorganism populations;
      modeling, by the control unit, the frequency of k-mers in the sequences sample that match the database using one or several probabilistic models per taxon;
      modeling, by the control unit, the distribution of frequency of the taxa-specific and taxa-unique k-mers found in unambiguously mapped sequence reads using one or more probabilistic models to estimate abundance of each identified one or more taxa, wherein the model utilizes a Poisson distribution or a mixture of probabilistic distribution from counts of occurrences of the taxa-specific and taxa-unique k-mers found in the unambiguously mapped reads to estimate the abundance of the one or more taxa;
      characterizing, based on the identified taxa, the pathogenicity of the one or more microorganism populations; and
   iii) administering to the subject a suitable treatment comprising an empiric antimicrobial therapy including one or more of antibiotics, antivirals, antifungals, antiprotozoals, and antihelminthics for eliminating the one or more microorganism populations based on the pathogenicity characterization; or cleaning the environmental source of the sample with an appropriately adjusted cleaning approach comprising specific cleaning products that appropriately eliminates the one or more microorganism populations based on the pathogenicity characterization rather than cleaning blindly.

15. The method of claim 14, wherein the probabilistic model increases confidence.

16. The method of claim 14, wherein the set of k-mers includes at least 10 individual k-mers.

17. The method of claim 14, wherein the set of k-mers includes at least 100 individual k-mers.

18. The method of claim 14, wherein the set of k-mers includes a plurality of k-mers each ranging from about 17 to about 63 nucleotides in length.

19. The method of claim 14, wherein the set of k-mers includes a plurality of k-mers each ranging from about 17 to about 31 nucleotides in length.

20. The method of claim 14, wherein a subset of the reference database is used that corresponds to the sample source, whether patient or environmentally collected, to increase confidence while maximizing analysis speed.

21. The method of claim 14, wherein the obtained sample comprises DNA or RNA.

22. The method of claim 14, wherein the one or more microorganism populations in the sample comprises one or more of *Clostridium difficile, Staphylococcus aureus* (including Methicillin resistant strains (MRSA)), *Klebsiella pneumoniae, Klebsiella oxytoca, Escherichia coli, Enterococcus* species (including *E. faecalis* and *E. faecium* and Vancomycin-resistant Enteroccus (VRE)), *Pseudomonas aeruginosa, Candida* species (including *C. albicans, C. parapsilosis*, and *C. glabrata*), *Streptococcus* species, Coagulase-negative *staphylococcus* species, *Enterobacter* species, *Acinetobacter baumannii, Proteus mirabilis, Stenotrophomonas maltophilia, Citrobacter species, Serratia species, Bacteroides species, Haemophilus* species, adenovirus, herpes simplex virus, parainfluenza virus and norovirus, *Peptostreptococcus* species, additional *Klebsiella* species, additional *Clostridium* species, *Prevotella* species, *Morganella morganii, Lactobacillus* species, Avian influenza virus, swine influenza virus, Zika virus, West Nile virus, Ebola virus, *plasmodium* species, yellow fever virus, Dengue virus, Lassa virus, Human immunodeficiency virus, *Vibrio cholerae*, Middle East respiratory syndrome coronavirus (MERS-COV), *Mycobacterium tuberculosis, Borrelia burgdorferi, Yersinia pestis*, or a virus causative of viral hepatitis.

* * * * *